United States Patent [19]

Jarreau et al.

[11] Patent Number: 5,036,091
[45] Date of Patent: Jul. 30, 1991

[54] 3-ARYLOXAZOLIDINONE DERIVATIVES, PROCESS FOR THEIR PREPARATION AND THEIR USE IN THERAPY

[75] Inventors: Francois X. Jarreau, Versailles; Vincenzo Rovei, Rueil Malmaison; Jean-Jacques Koenig, Maisons Laffitte; Alain R. Schoffs, Paris, all of France

[73] Assignee: Delalande S.A., Courbevoie, France

[21] Appl. No.: 597,583

[22] Filed: Oct. 15, 1990

[30] Foreign Application Priority Data

Oct. 17, 1989 [FR] France ................. 8913555

[51] Int. Cl.$^5$ .................. C07D 263/24; A61K 31/42
[52] U.S. Cl. ........................ 514/376; 548/232
[58] Field of Search .................. 548/232; 514/376

[56] References Cited

U.S. PATENT DOCUMENTS 4,338,451 7/1982 Doslert et al. ............. 548/232
4,517,197 5/1985 Ancher et al. ............. 548/232

Primary Examiner—Mary C. Lee
Assistant Examiner—Peter Davis
Attorney, Agent, or Firm—Zarley, McKee, Thomte, Voorhees, & Sease

[57] ABSTRACT

The derivatives of the formula:

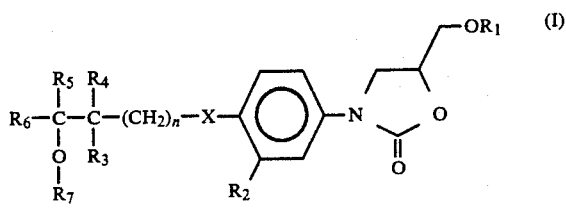

wherein:
$R_1$ is H or $C_1$-$C_4$ alkyl;
X is either an oxygen atom, in which case $R_2$=H or halogen, or a methylene group or a —CH=CH— group, in which case $R_2$=H;
n is 1 or 2 when X is an oxygen atom or a methylene group and 0 or 1 when X is a —CH=CH— group;
each of $R_3$ and $R_4$ is independently H, $C_1$-$C_4$ alkyl, $C_4$-$C_7$ cycloalkyl, phenyl or benzyl;
$R_5$ is H or $C_1$-$C_4$ alkyl;
$R_6$ is $C_1$-$C_4$ alkyl, $CHF_2$, $CF_3$, $CF_3CH_2$, $C_4$-$C_7$ cycloalkyl, phenyl or benzyl;
$R_4$ and $R_6$ may further form together a —$(CH_2)_3$— or —$(CH_2)_4$— chain;
$R_5$ and $R_6$ may further form together a —$(CH_2)_4$— or —$(CH_2)_5$— chain; and
$R_7$ is H, $C_1$-$C_4$ alkyl, $C_2$-$C_5$ acyl or benzyl,
useful as drugs.

9 Claims, No Drawings

3-ARYLOXAZOLIDINONE DERIVATIVES, PROCESS FOR THEIR PREPARATION AND THEIR USE IN THERAPY

The present invention relates to new 3-aryl-2-oxazolidinone derivatives, to a process for their preparation and to their use in therapy.

More precisely, these derivatives correspond to the formula:

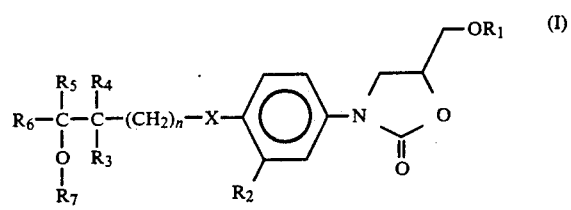

wherein:
- $R_1$ is H or $C_1$-$C_4$ alkyl;
- X is either an oxygen atom, in which case $R_2$=H or halogen, or a methylene group or a —CH=CH— group, in which case $R_2$=H;
- n is 1 or 2 when X is an oxygen atom or a methylene group and 0 or 1 when X is a —CH=CH— group;
- each of $R_3$ and $R_4$ is independently H, $C_1$-$C_4$ alkyl, $C_4$-$C_7$ cycloalkyl, phenyl or benzyl;
- $R_5$ is H or $C_1$-$C_4$ alkyl;
- $R_6$ is $C_1$-$C_4$ alkyl, $CHF_2$, $CF_3$, $CF_3CF_2$, $C_4$-$C_7$ cycloalkyl, phenyl or benzyl;
- $R_4$ and $R_6$ may further form together a —$(CH_2)_3$— or —$(CH_2)_4$— chain;
- $R_5$ and $R_6$ may further form together a —$(CH_2)_4$— or —$(CH_2)_5$— chain; and
- $R_7$ is H, $C_1$-$C_4$ alkyl, $C_2$-$C_5$ acyl or benzyl.

It should be moreover noted that the derivatives (I) include one or more asymmetric carbon atoms. They can therefore be under the form of diastereoisomers or enantiomers or under the cis- or trans-form or also under the form of a mixture of all theses forms, including the racemic forms. The present invention therefore encompasses the various forms so defined.

The above formula (I) particularly encompasses the derivatives for which:
- $R_1$=H or $CH_3$;
- $R_2$=H;
- X=oxygen or $CH_2$;
- n=1 or 2;
- $R_3$, $R_4$ and $R_5$ are H or $CH_3$;
- $R_6$ is $CH_3$ or $CF_3$; and
- $R_7$ is H, $CH_3$ or acetyl.

The derivatives for which:
- $R_1$=$CH_3$;
- $R_2$=H;
- X=oxygen;
- n=1 or 2;
- $R_3$=$R_4$=$R_5$=H;
- $R_6$=$CF_3$; and
- $R_7$=H;

| the derivatives for which: | the derivatives for which: |
| --- | --- |
| $R_1$ = $CH_3$; | $R_1$ = $CH_3$; |
| $R_2$ = H; | $R_2$ = H; |
| X = methylene; | X is CH = CH; |
| n = 1 or 2; | n is 0 or 1; |
| $R_3$ = $R_4$ = $R_5$ = H; | $R_3$ = $R_4$ = $R_5$ = H; |
| $R_6$ = $CF_3$; and | $R_6$ = $CF_3$; and |
| $R_7$ = H; and | $R_7$ = H, | are particularly mentioned.

The present invention moreover relates to the preparation processes of derivatives (I).

These processes are mainly based on two general synthetic routes.

The first one of these routes comprises creating an entity including the 2-oxazolidinone moiety (schemes 1 and 2), following by grafting on this entity the chain including the

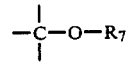

residue (schemes 3 and 4) or a precursor group of

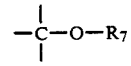

(scheme 5).

Conversely, the second one of these routes comprises firstly creating the chain including the

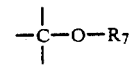

residue (schemes 6 and 7) or a precursor group of

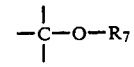

(schemes 8 and 9), followed by creating and grafting on this chain an entity including the 2-oxazolidinone moiety (schemes 10, 11 and 12).

These twelve schemes are represented below. Unless otherwise stated, the symbols $R_1$, $R_2$, X, n, $R_4$, $R_3$, $R_5$, $R_6$ and $R_7$ appearing in these schemes have the same meanings as in formula (I).

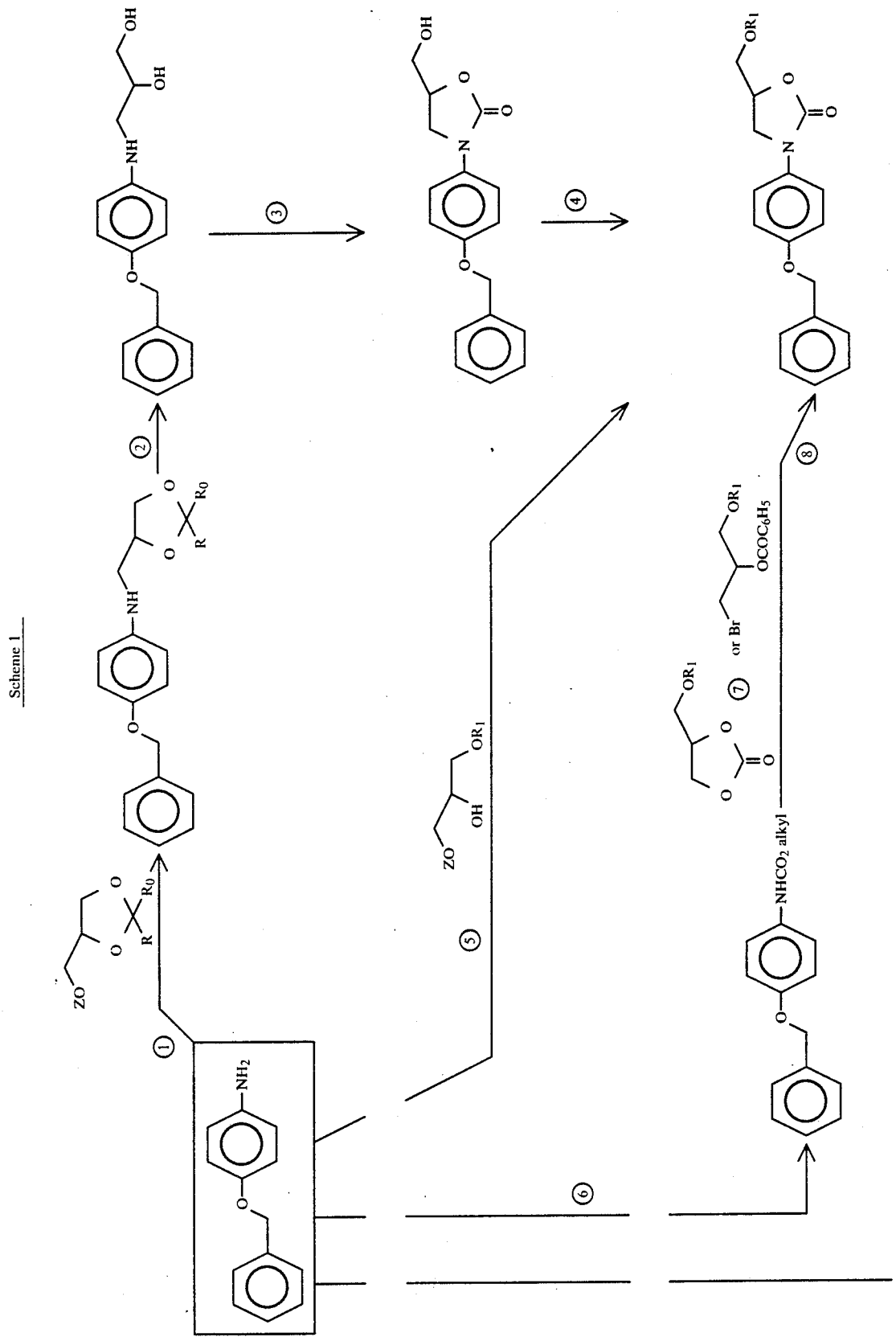
Scheme 1

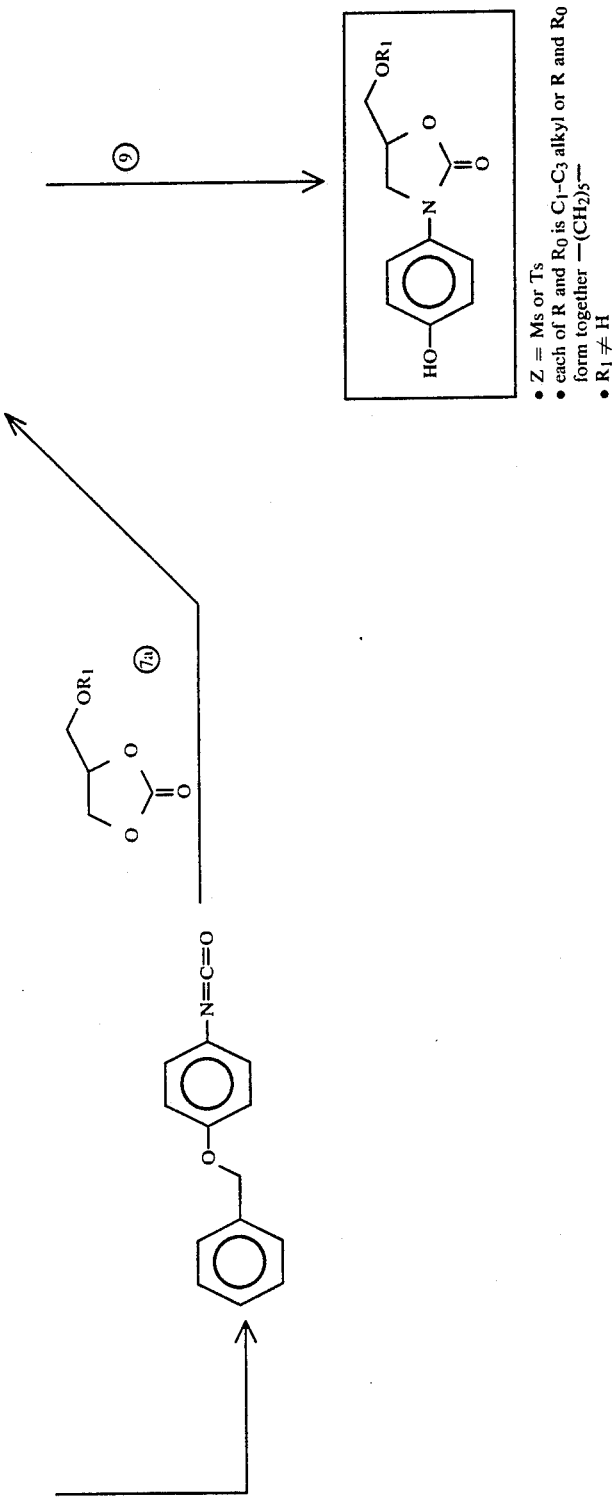

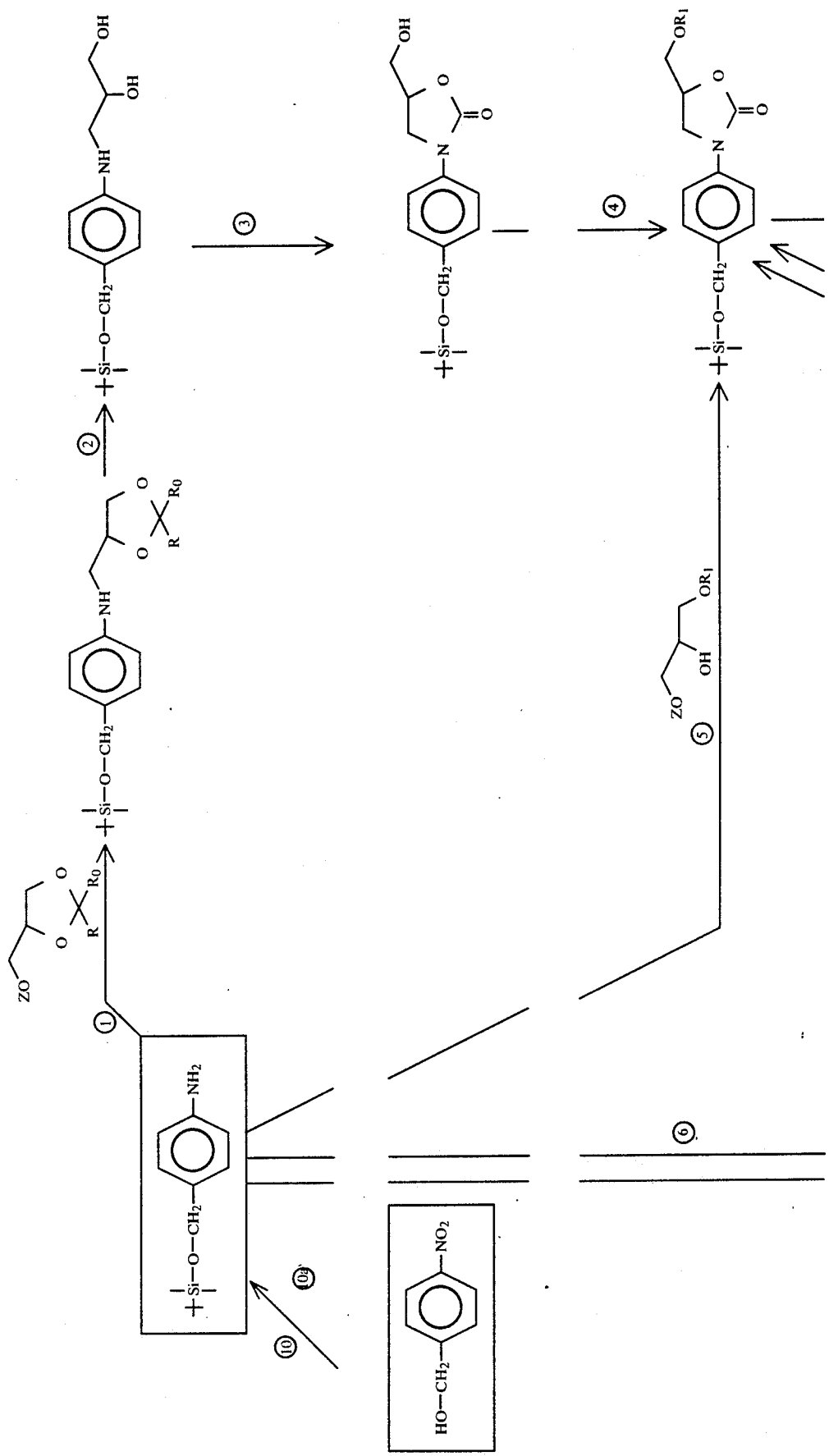
Scheme 2

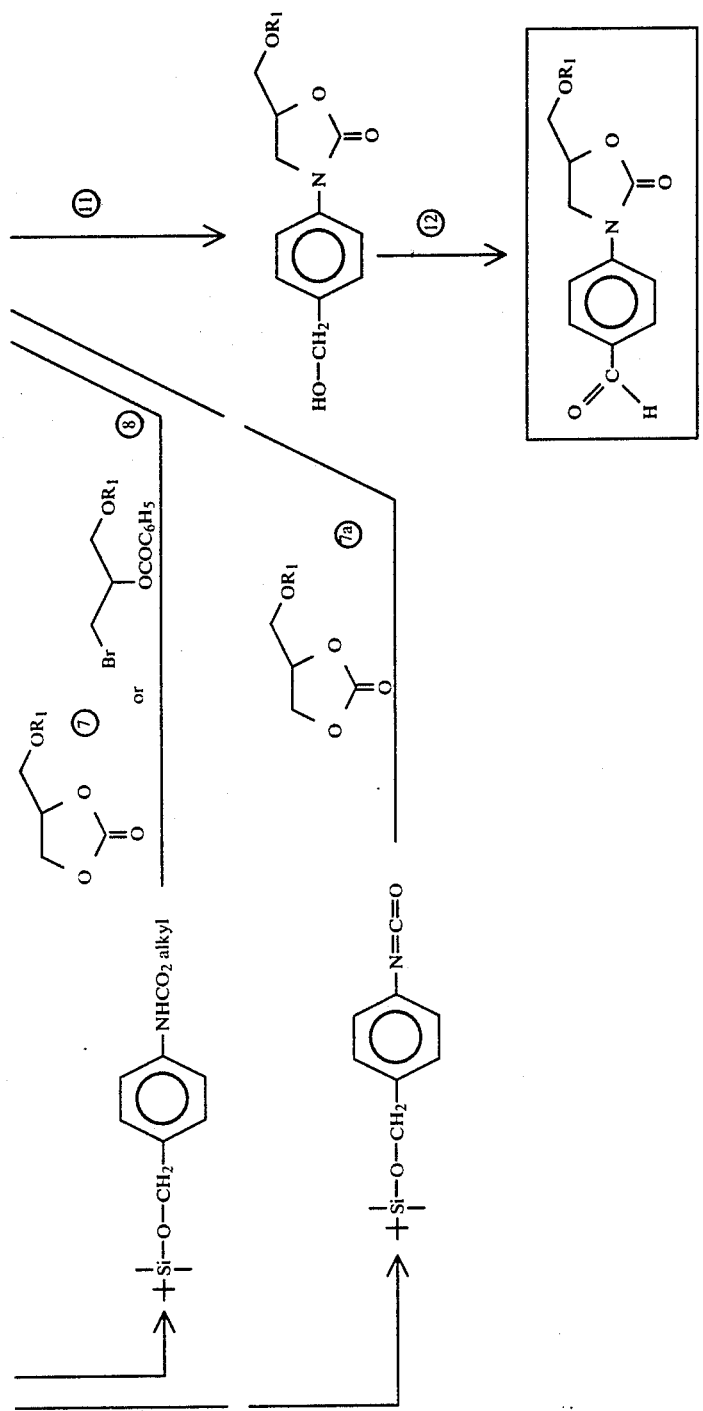
- $Z$ = Ts or Ms
- each of R and $R_0$ is $C_1-C_3$ alkyl or R and $R_0$ form together $-(CH_2)_5-$
- $R_1 \neq H$

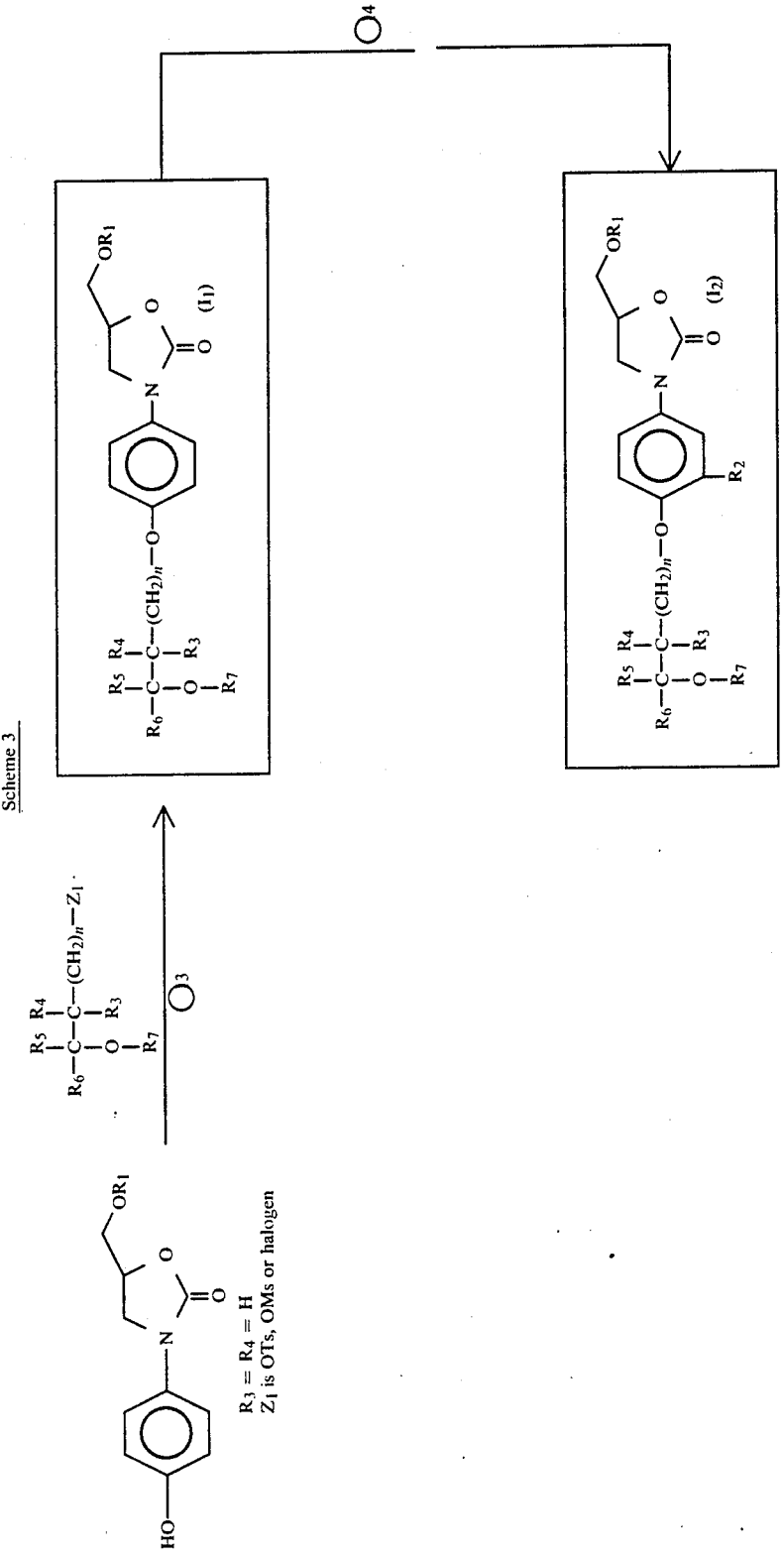

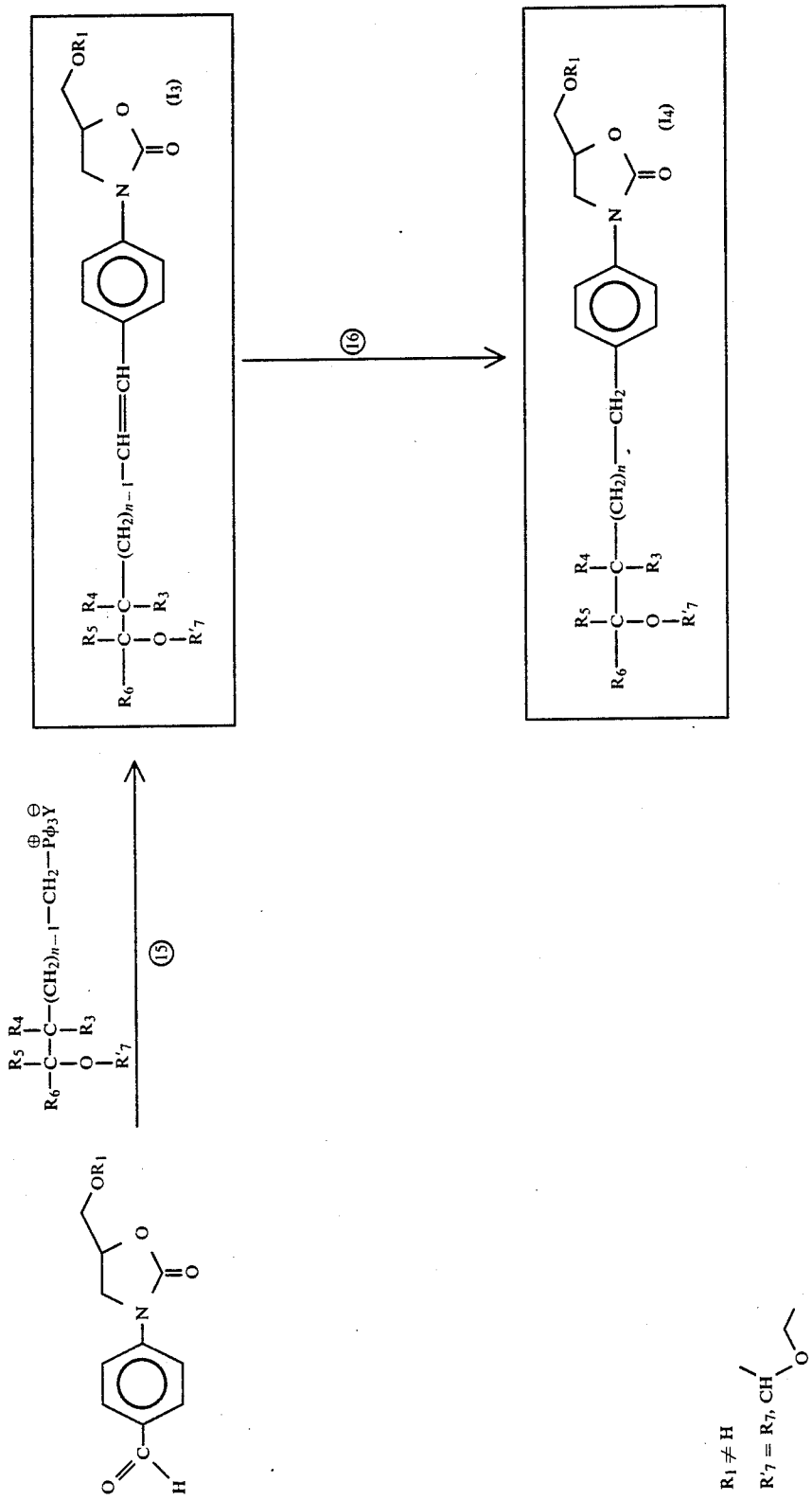

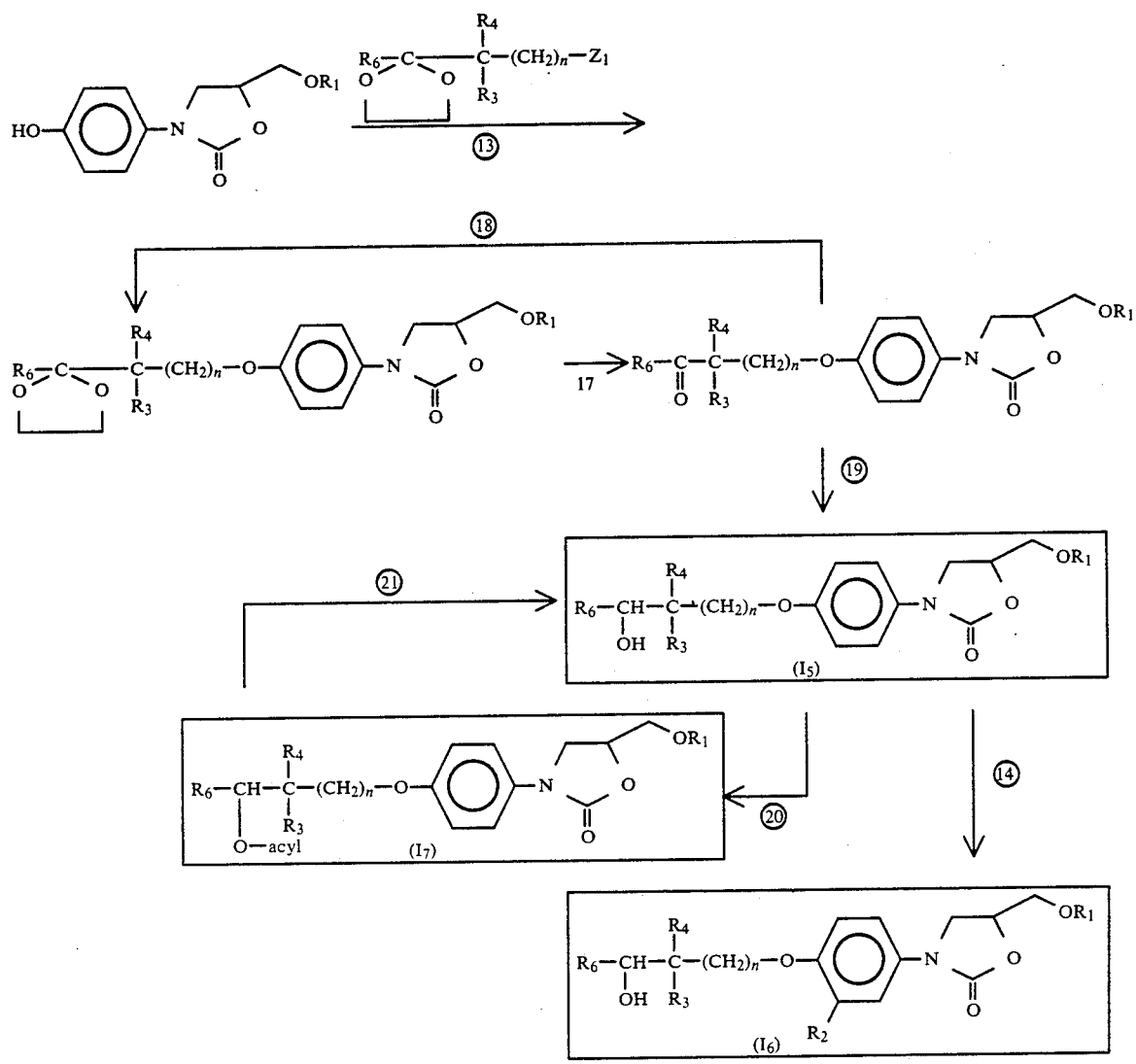
Scheme 5
$Z_1$ = TsO, MsO, halogen
$R_6$ = CHF$_2$, CF$_3$, CF$_3$CF$_2$
$R_2$ = halogen
Scheme 6
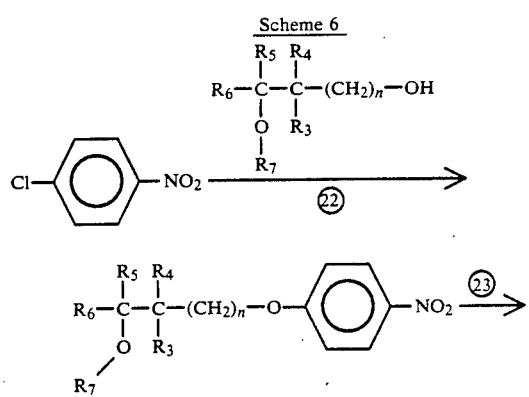
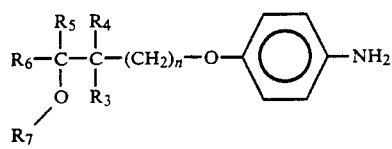
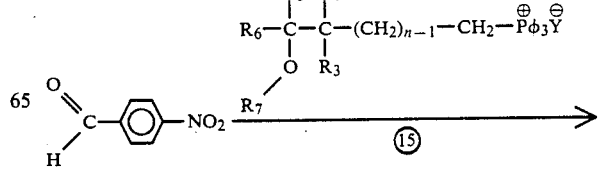
Scheme 6

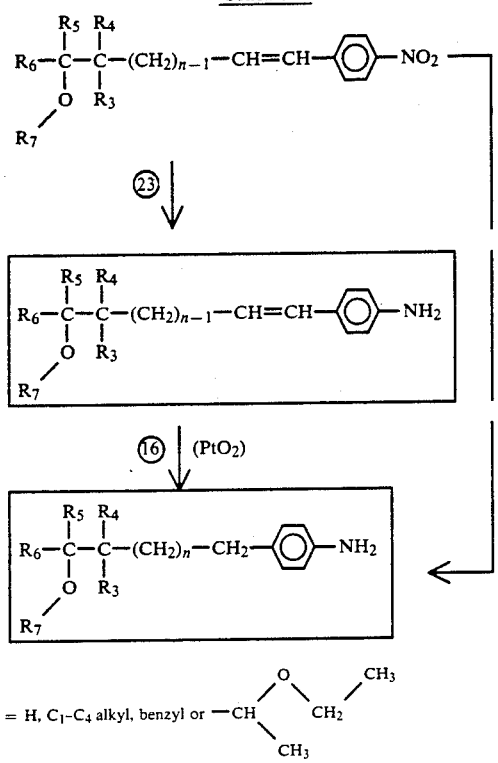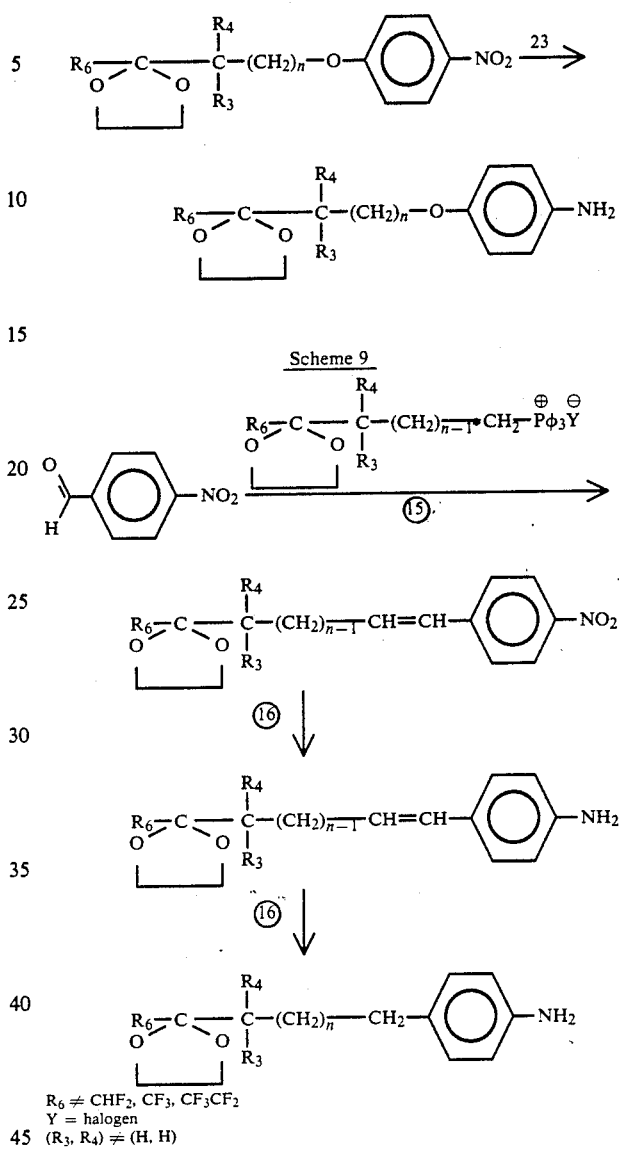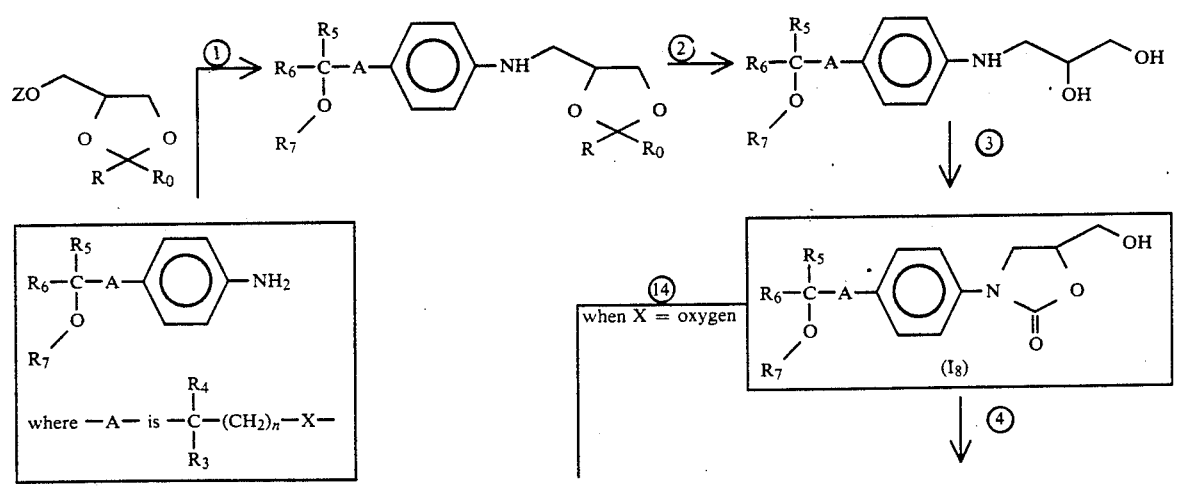

-continued
Scheme 10
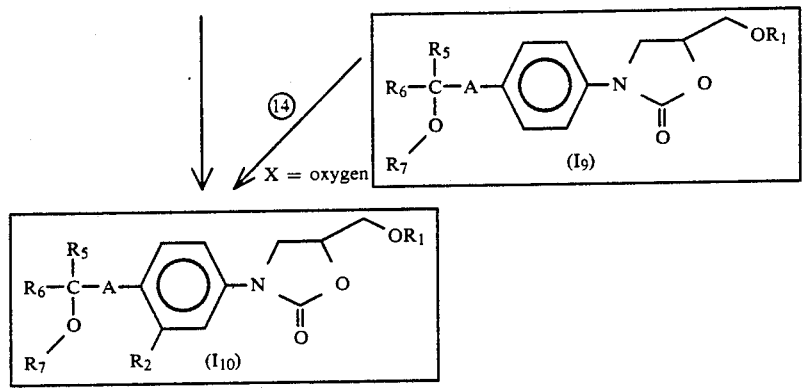
Z = Ts or Ms
$R_1 \neq H$
$R_7 \neq$ acyle
each of R and $R_0$ is $C_1$-$C_4$ alkyl or R and $R_0$ form together a $-(CH_2)_5-$ chain
$R_2$ = halogen
Scheme 11
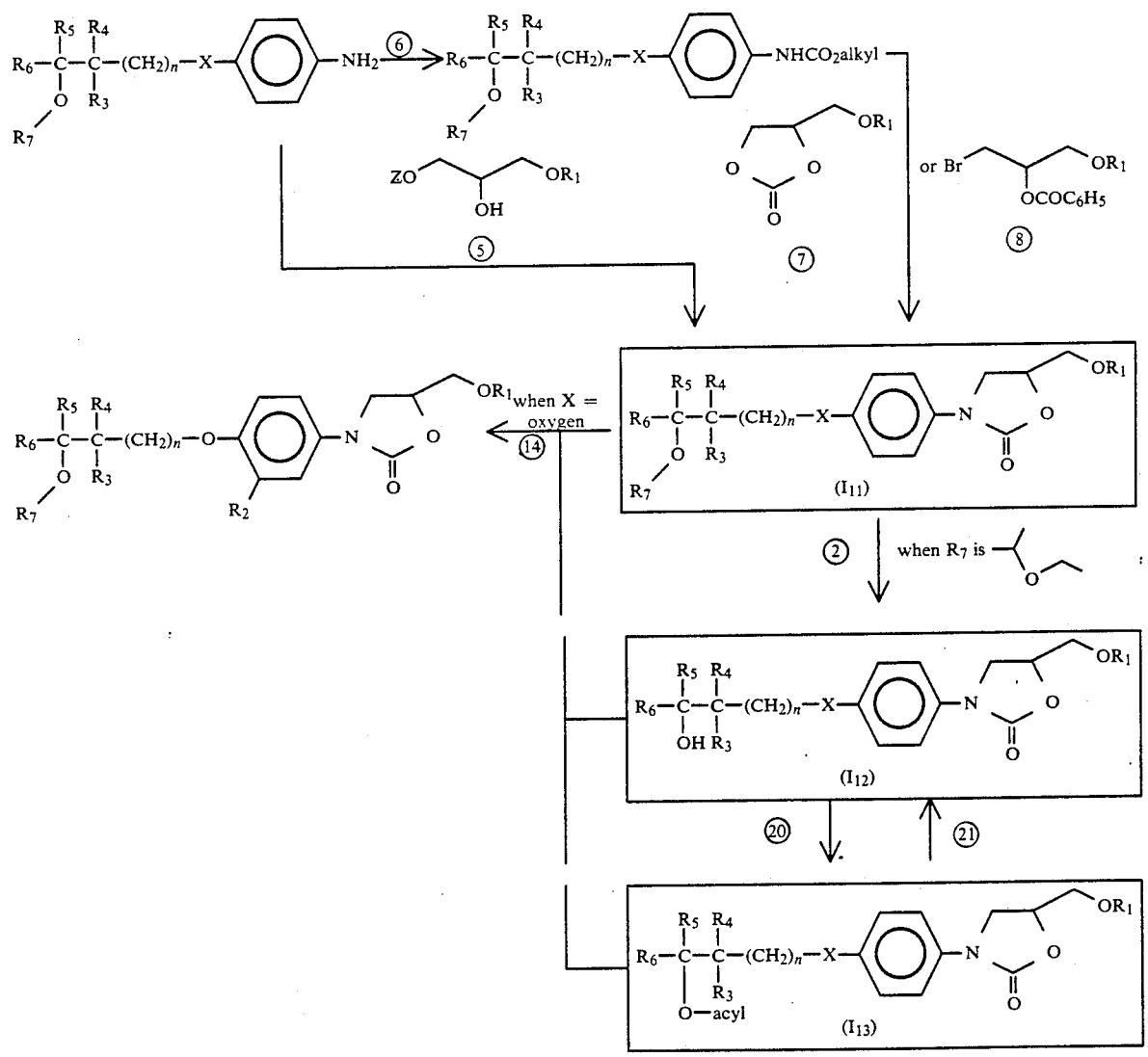

-continued
Scheme 11
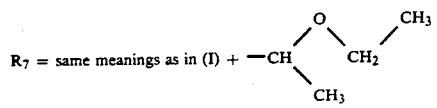
$R_1 \neq H$
$R_2$ = halogen
$Z$ = Ts or Ms

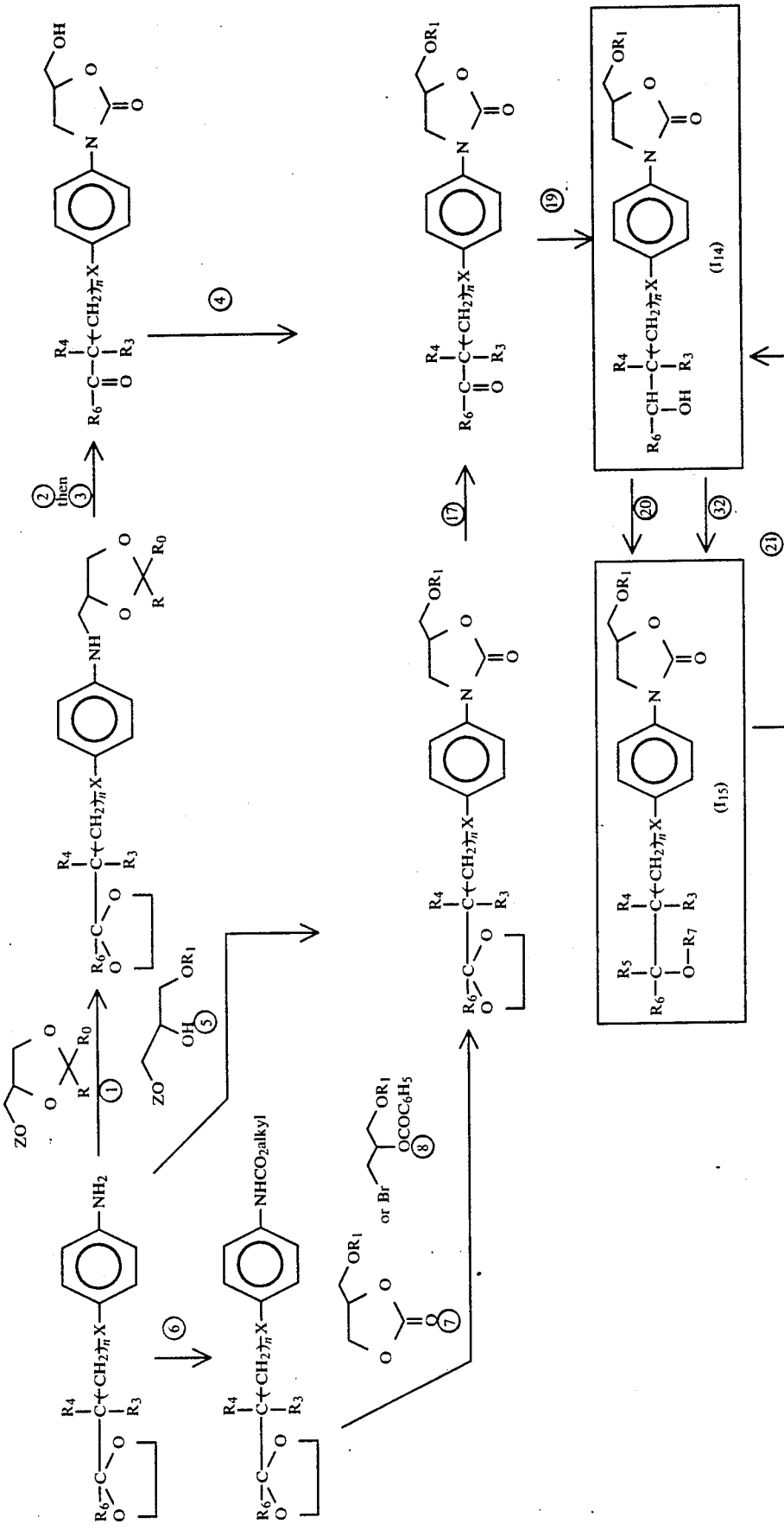
Scheme 12
$R_1 \neq H$
$Z = Ts, Ms$
$R_6 \neq CHF_2, CF_3, CF_3CF_2$
$R_7 = $ acyl, $C_1-C_4$ alkyl or benzyl Moreover, the compounds of formulae:
are obtained according to scheme 13 represented below.
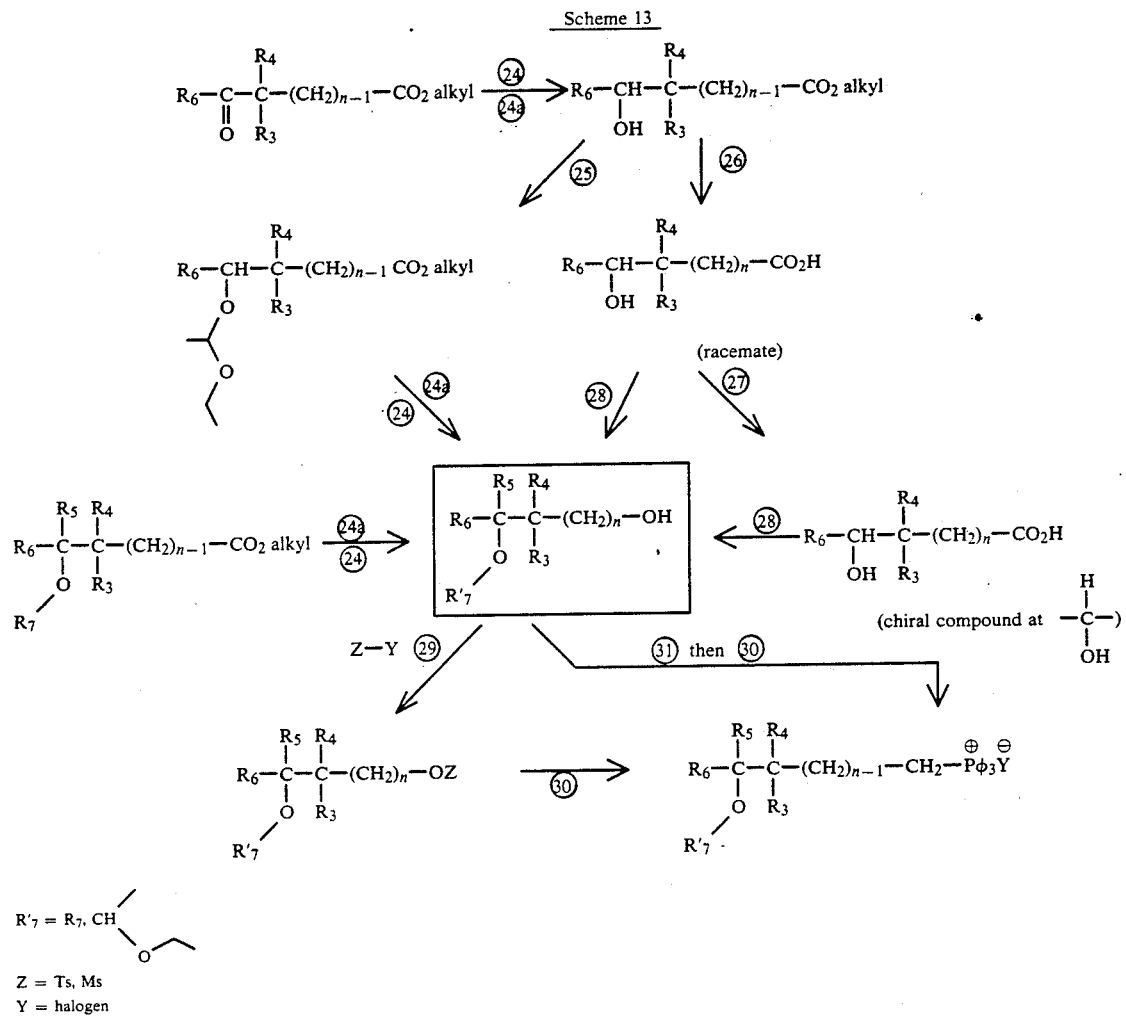
Scheme 13
$R'_7 = R_7, CH\diagdown_O\diagup$
Z = Ts, Ms
Y = halogen
Moreover, the compounds of formulae:
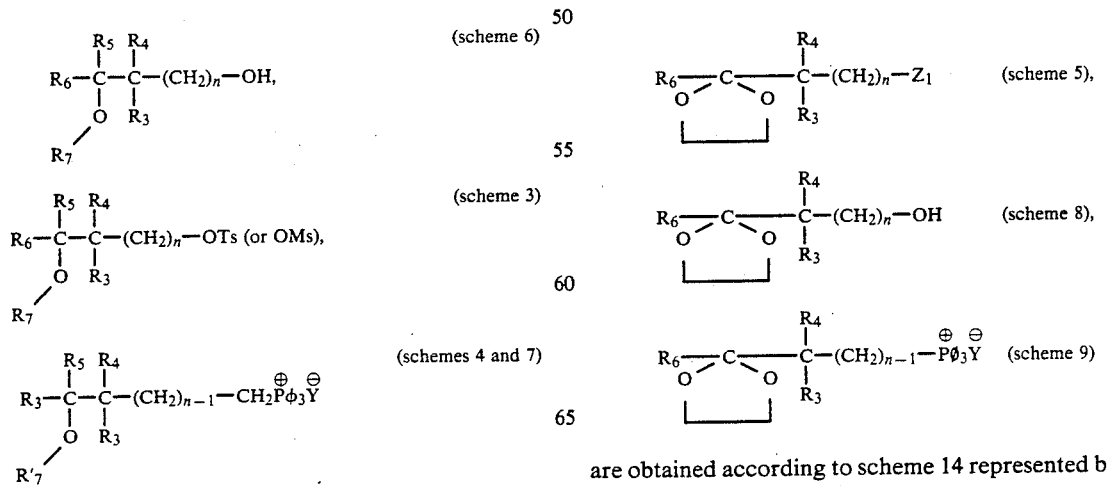
(scheme 6)
(scheme 3)
(schemes 4 and 7)
(scheme 5),
(scheme 8),
(scheme 9)
are obtained according to scheme 14 represented below.

Scheme 14

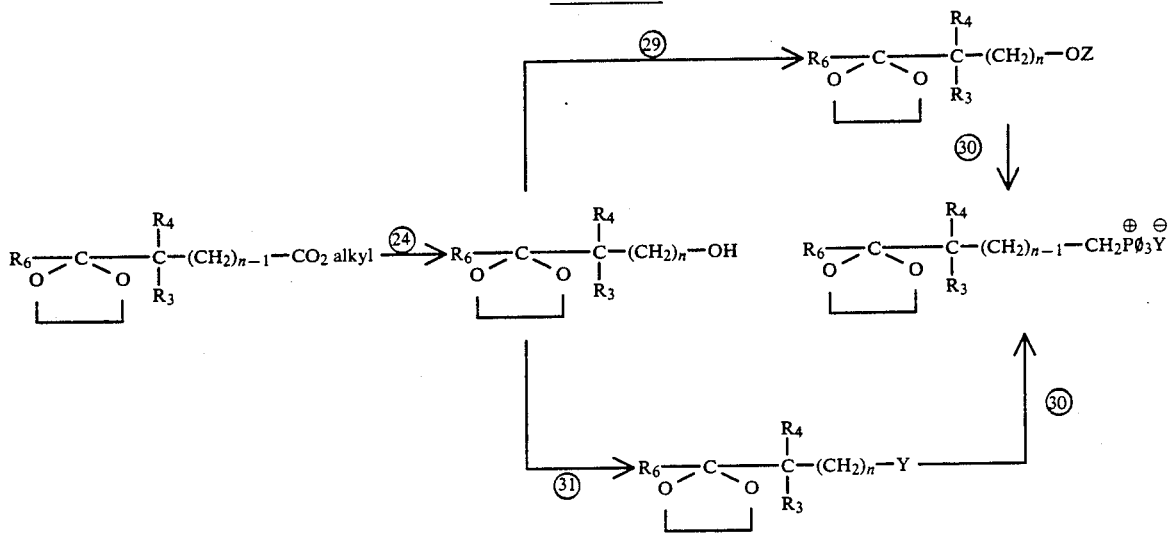

Z = Ts, Ms
Y = halogen

The ① to ㉜ numbers appearing in the above schemes have the following meanings:

① Condensation either in an anhydrous aprotic solvent like toluene, by heating, with or without a catalyst like hexadecyl tributyl phosphonium bromide or a quaternary ammonium halogenide such as benzyl triethylammonium bromide, or without a solvent in the presence of triethylamine between 130°-150° C.

② Hydrolysis with an aqueous acid, particularly 6N hydrochloric acid, in the presence of an organic solvent like methylethylketone or ethyl ether.

③ Condensation with a $C_1$-$C_4$ alkyl carbonate, particularly, diethyl carbonate, in an anhydrous solvent like toluene in the presence of an alkali metal alkoxide like sodium methoxide.

④ Alkylation with a $C_1$-$C_4$ alkyl halogenide (bromide or chloride) in phase transfer conditions, particularly sodium hydroxide-methylene chloride or toluene, in the presence of a quaternary ammonium like tetrabutylammonium bromide or hydrogen sulphate.

⑤ Condensation in the presence of phosgene and a base, particularly dimethylaniline, in an organic solvent like methylene chloride or dichloroethane; and then ring formation by heating in an organic solvent particularly an alcoholic solvent like ethanol in the presence of a base, particularly potassium hydroxide.

⑥ Condensation with an alkyl chloroformate, like ethyl chloroformate, in the presence of a base, particularly $NaHCO_3$, in a solvent mixture water-THF, at room temperature.

⑦ Condensation with heating (about 150° C.) in the presence of a base like $K_2CO_3$. The reaction retains the stereochemistry.

⑦ₐ Condensation in toluene in the presence of LiBr and $nBu_3PO$.

⑧ Condensation in the presence of a base, particularly NaH, in an aprotic solvent like THF, at 55° C.-60° C.

⑨ Debenzylation in an alcoholic solvent like methanol or ethanol, in the presence of hydrogen and a catalyst, particularly 10% palladium-carbon, humidified or not.

⑩ O-silylation of the alcohol in an aprotic organic solvent like THF, in the presence of a base, particularly imidazole, and of terbutyldimethylchlorosilane.

⑩ₐ Reduction of the nitro derivative with powdered iron in the presence of ammonium chloride.

⑪ Hydrolysis in an organic solvent, particularly THF, in the presence of a fluoride, particularly tetrabutylammonium fluoride.

⑫ Oxidation in the presence of oxalyl chloride, DMSO and a base, particularly triethylamine, in an aprotic organic solvent like methylene chloride.

⑬ O-alkylation in an anhydrous aprotic organic solvent like methylethylketone or DMF, and in the presence of a base, particularly, $K_2CO_3$, or O-alkylation in an aprotic organic solvent like DMF and/or THF, and in the presence of an alkali metal hydride, like sodium hydride.

⑭ Halogenation by the action of a halogen in acetic acid.

⑮ Condensation in the presence of a base particularly $K_2CO_3$, and of formamide in an aprotic solvent, particularly dioxane, preferably under reflux, or Condensation in the presence of LDA (lithium diisopropylamide) in a solvent mixture, particularly DMSO/THF.

⑯ Hydrogenation under atmospheric pressure of hydrogen in an organic solvent, particularly ethyl acetate, in the presence of a catalyst, like 10% palladium-carbon, humidified or not, or $PtO_2$ or Hydrogenation under hydrogen pressure, particularly under 5 atm, in the presence of 10% palladium-carbon, humidified or not, or $PtO_2$, in an alcoholic solvent, particularly ethanol, or Hydrogenation under hydrogen pressure, particularly under 9 atm, in the presence of 10% palladium-carbon, humidified or not, in an alcoholic solvent, particularly ethanol.

⑰ Hydrolysis in the presence of silica and iron chloride hydrate in an organic solvent, particularly acetone or methylethylketone.

(18) Acetalisation in the presence of aminopropyl grafted silica in the form of hydrochloride, with ethylene glycol, in an aprotic solvent, particularly methylene chloride and with or whithout ethyl orthoformate, or Acetalisation with ethylene glycol, under reflux of an aprotic solvent, particularly toluene, in the presence of paratoluene sulfonic acid, while removing the water formed.

(19) Reduction with an alkali metal borohydride (for example Na) in an alcoholic solvent (for example EtOH).

(20) Acylation, for example
Action of an alkyl-COOH acid anhydride, in an organic solvent like $CH_2Cl_2$, in the presence of a base like pyridine, or
Action of an alkyl-COOH acid in the presence of triphenylphosphine and ethyl azodicarboxylate, in an organic solvent like THF (inversion of the stereochemistry).

(21) Basic hydrolysis in an organic solvent, particularly EtOH or MeOH, with a base like NaOH or KOH.

(22) O-alkylation in an aprotic organic solvent, particularly DMF or THF, in the presence of alkali metal hydride, particularly sodium hydride.

(23) Reduction of the nitro derivative by powdered iron in the presence of ammonium chloride.

(24) Reduction in an aprotic organic solvent like dimethoxyethane or $CH_2Cl_2$, in the presence of sodium or lithium borohydride.

(24a) Reduction with $AlLiH_4$ in an aprotic solvent like THF.

(25) O-alkylation with ethylvinylether in the presence of a catalytic amount of $POCl_3$, in an aprotic solvent like $CH_2Cl_2$.

(26) Saponification with an alkaline base like NaOH in an alcoholic solvent like EtOH.

(27) Formation of a chiral salt with (R) or (S) α-methylbenzylamine, and then separation of the diastereoisomers formed, and releasing of the chiral acid with an acid, particularly HCl.

(28) Reduction with an alkali metal borohydride (for example Na), in the presence of $BF_3$ etherate in an aprotic solvent, particularly THF, or with bis (methoxyethoxy) aluminum sodium hydride [$(CH_3OCH_2CH_2O)_2AlH_2Na$] in toluene.

(29) Condensation in an organic solvent, particularly pyridine, THF or $CH_2Cl_2$, in the presence of a base, particularly 4-dimethylamino pyridine or $Et_3N$.

(30) According to Helv. Chim. Acta 59. 755 (1976).

(31) According to Can. J. Chem. 1968, 46, 86.

(32) O.alkylation with a $C_1$-$C_4$ alkyl halogenide or sulphate, or benzyl halogenide, preferably either in an aprotic organic solvent like DMF and in the presence of a metal hydride, particularly NaH, or in phase transfer conditions in the presence of a catalyst like tertiobutylammonium bromide in a toluene/50% aqueous NaOH mixture.

The following preparations are given by way of examples for illustrating the invention.

EXAMPLE 1

Racemic mixture of diastereoisomers of 3-[4-(3-hydroxybutoxy)phenyl]-5-methoxymethyl-2-oxazolidinone (code number MD 370047)

To a solution of 27.5 g (0.112 mol) of 1-tosyloxy-3-butanol in 250 ml of methylethylketone, are added 28.2 g (0.2 mol) of $K_2CO_3$ and 22.8 g (0.102 mol) of 3-(4-hydroxyphenyl)-5-methoxymethyl-2-oxazolidinone (code number MD 780232). The mixture is heated under reflux for 4 h 30. After filtration and concentration, the residue is taken up in 200 ml of $CH_2Cl_2$, the organic phase is washed with NaCl saturated water, dried over $Na_2SO_4$ and concentrated. After purification by flash chromatography silica, eluent: $CH_2Cl_2$: 98; $CH_3OH$: 2), the aimed product is obtained with a 70% yield, m.p.: 58° C.;

$^1H$ NMR ($CDCl_3$) δ ppm: 1.2 (3H); 1.8 (2H); 2.5 (1 exch. H); 3.4 (3H); 3.6 (2H); 3.7–4.2 (5H); 4.7 (1H); 6.8 (2H); 7.4 (2H);

IR (KBr) ν $cm^{-1}$: 3400, 1750, 1730.

In the same manner, but starting from 4,4,4-trifluoro-1-tosyloxy-3-butanol and 3-(4-hydroxyphenyl)-5-methoxymethyl-2-oxazolidinone (code number MD 780232), there was obtained the mixture of racemic diasteroisomers:

3-[4-(4,4,4-trifluoro-3-hydroxybutoxy)phenyl]-5-methoxymethyl-2-oxazolidinone: (code number MD 370167);

m.p.: 89° C., $^1H$ NMR ($CDCl_3$) δ ppm: 2.05 (2H); 3.4 (3H); 3.5 (1 exch. H); 3.6 (2H); 3.7–4.3 (5H); 4.7 (1H); 6.8 (2H); 7.3 (2H).

IR (KBr) ν $cm^{-1}$: 3400, 1750, 1785.

EXAMPLE 2

3-[4-(3(R)-hydroxybutoxy)phenyl]-5(R)-methoxymethyl-2-oxazolidinone (code number 370120)

Step 1: 3-(4-benzyloxyphenyl)aminopropane-1,2(R)-diol (code number MD 200418)

In an autoclave 1.5 kg of 4-benzyloxyaniline (7.564 mol), 201.4 g of 1,4-dioxaspiro[4,5]decane-2-methanol (S)mesylate (8.048 mol) and 1.88 l of triethylamine (13.5 mol) are added. The reagents are heated at 140° C. for 30 min. The reaction medium is then taken up in 7 l of methylethylketone. The solution is washed with water and used for the subsequent step. To this solution, 1.2 l of 36% hydrochloric acid are added. The reaction medium is heated at 55° C. for 30 min. and cooled at 20° C. Soda lye is added until pH 9 is reached. The organic solution is washed with water and concentrated.

The product is obtained with a 90% yield;

m.p.: 102° C.; $[α]_D^{20}$ = +12.7° (c=1, $CH_3OH$).

Step 2: 3-(4-benzyloxyphenyl) 5(R)-methoxymethyl-2-oxazolidinone (code number MD 200404)

(a) To a suspension of 13 g (0.0475 mol) of compound MD 200418 in 100 ml of toluene, are added under reflux 6.2 ml (0.052 mol) of ethyl carbonate and 2 ml of 1M methanolic sodium methoxide. A distillation is carried out until the reflux reaches the boiling point of toluene. After cooling, $CH_2Cl_2$ is added and the organic solution is washed with water and dried over $Na_2SO_4$. After concentration, 14 g of 3-(4-benzyloxyphenyl)-5(R)-hydroxymethyl-2-oxazolidinone (code number MD 220201) are obtained:

m.p.: 157° C.; $[α]_D^{20}$ = −41° (c=1, $CH_2Cl_2$).

(b) To 15 g (0.05 mol) of the previously obtained product (MD 220201), are added 100 ml of toluene and 18.9 g of methyl sulphate, 1.8 g of tetrabutylammonium hydrogen sulphate, 10 ml of water and 10 g of NaOH. The reagents are heated for ½ h. The reaction medium is extracted with isopropyl ether and the aimed product is obtained with a 83% yield;

m.p.: 101° C.; $[α]_D^{20}$ = −41.5° (c=1, $CH_2Cl_2$).

Using the same procedure but starting from the suitable reagents, there were obtained
3-(4-benzyloxy-phenyl)-5(S)-methoxymethyl-2-oxazolidinone (code number 340190): m.p.: 101° C.; $[\alpha]_D^{20} = +41.9°$ (c=1, $CH_2Cl_2$),
as well as
3-(4-benzyloxyphenyl)-5(R)-ethoxymethyl-2-oxazolidinone (code number MD 230242): m.p.: 78° C.; $[\alpha]_D^{20} = -35.9°$ (c=1, $CH_2Cl_2$); IR (KBr) $\nu$ cm$^{-1}$: 1750, 1735.

Step 3: 3-(4-hydroxyphenyl)-5(R)-methoxymethyl-2-oxazolidinone (code number MD 200405)

To a solution of 13 g (0.047 mol) of the compound MD 200404 in 80 ml of ethanol and 40 ml of $CH_2Cl_2$ in the presence of 2.6 g of 50% humidified 10% Pd/C, a hydrogen stream is passed through under normal pressure.

After completion of the reaction, the solution is filtered and concentrated. The aimed product is obtained with a 100% yield.
m.p.: 112° C.; $[\alpha]_D^{20} = -67°$ (c=1, $CH_3OH$);
IR (KBr) $\nu$ cm$^{-1}$: 3260, 1730.

Using the same process but starting from the corresponding reagents, there were obtained
the 3-(4-hydroxyphenyl)-5(S)-methoxymethyl-2-oxazolidinone derivative (code number MD 200717):
m.p.: 114° C.; $[\alpha]_D^{20} = +66°$ (c=1, $CH_3OH$),
as well as
the 3-(4-hydroxyphenyl)-5(R)-ethoxymethyl-2-oxazolidinone derivative (code number MD 230243):
m.p.: 92° C.; $[\alpha]_D^{20} = -58.9°$ (c=1, $CH_3OH$). IR (KBr) $\nu$ cm$^{-1}$: 3300, 1770.

Step 4: 3-[4-(3(R)-hydroxybutoxy)phenyl]-5(R)-methoxymethyl-2-oxazolidinone (code number MD 370120)

To 100 ml of methylethylketone, are added 14.6 g (0.059 mol) of 1-tosyloxy-3(R)-butanol (Helv. Chim. Acta, 67, 89, 1984), 14.8 g (0.1 mol) of $K_2CO_3$ and 18 g (0.053 mol) of compound MD 200405. The mixture is heated under reflux 5 h, after filtration, the reaction medium is concentrated, taken up in ethyl acetate, washed with water, dried over $Na_2SO_4$ and concentrated. The product is purified by flash chromatography (silica, eluent: $CH_2Cl_2$: 95; $CH_3OH$: 5);
m.p.: 76° C. $[\alpha]_D^{20}$: $-50.7°$ (c=1, $CH_2Cl_2$).

Using the same procedure, but reacting 1-tosylate-3(R)-butanol with compound MD 200717, there is obtained:
3-[4-(3(R)-hydroxybutoxy)phenyl]-5(S)-methoxymethyl-2-oxazolidinone (code number MD 370123): m.p.: 44° C., $[\alpha]_D^{20}$: $+33°$ (c=1, $CH_2Cl_2$).

Likewise, there are obtained by reacting 1-tosyloxy-3(S)-butanol (J. Org. Chem. 47, 3850, 1982) with compound MD 200405
3-[4-(3(S)-hydroxybutoxy)phenyl]-5(R)-methoxymethyl-2-oxazolidinone (code number MD 370122),
and with compound MD 200717,
3-[4-(3(S)-hydroxybutoxy)phenyl]-5(S)-methoxymethyl-2-oxazolidinone (code number MD 370121).

EXAMPLE 3

3-[4-(3(S)-hydroxybutoxy)phenyl]-5(S)-methoxymethyl-2-oxazolidinone (code number MD 370121)

Step 1: 3-[4-(3(S)-acetoxybutoxy)phenyl]-5(S)-methoxymethyl-2-oxazolidinone (code number MD 370162)

6.5 g ($2.2 \times 10^{-2}$ mol) of the compound having code number 370123 (Ex. 2, Step 4) and 17.3 g ($6.6 \times 10^{-2}$ mol) of triphenylphosphine are dissolved in 65 ml of THF cooled at 0° C.; a solution of ethyl diethylazodicarboxylate in 20 ml of THF is dropwise added within 20 min., and then 7.42 ml of acetic acid in 20 ml of THF. The mixture is left under stirring for 2 hours. After concentration, the product is purified by flash chromatography (silica, eluent: AcOEt; 50; Heptane: 50);
m.p.<50° C.; $[\alpha]_D^{20} = +52.8°$ (c=1, $CH_2Cl_2$);
IR film $\nu$ cm$^{-1}$): 1760, 1740.
$^1$H NMR (CDCl$_3$) $\delta$ ppm: 1.3 (3H); 2 (5H); 3.4 (3H); 3.6 (2H); 3.7–4.2 (4H); 4.7 (1H); 5.1 (1H); 6.8 (2H); 7.2 (2H).

In the same manner, the following compounds are obtained from the corresponding starting materials:
3-[4-(3(S)-acetoxybutoxy)phenyl]-5(R)-methoxymethyl-2-oxazolidinone (code number MD 370161): $[\alpha]_D^{20} = -18.6°$ (c=1, $CH_2Cl_2$).
3-[4-(3(R)-acetoxybutoxy)phenyl]-5(R)-methoxymethyl-2-oxazolidinone (code number MD 370220):
$^1$H NMR (CDCl$_3$) $\delta$ ppm: 1.3 (3H); 2 (5H); 3.4 (3H); 3.6 (2H); 3.7–4.2 (4H); 4.7 (1H); 5.1 (1H); 6.8 (2H); 7.4 (2H);
IR (KBr, $\nu$ cm$^{-1}$): 1730, 1740;
$[\alpha]_D^{20} = -53.1°$ (c=1, $CH_2Cl_2$); m.p.=43° C.
3-[4-(3(R)-acetoxybutoxy)phenyl]-5(S)-methoxymethyl-2-oxazolidinone (code number MD 370219):
$^1$H NMR (CDCl$_3$) $\delta$ ppm: 1.3 (3H); 2 (5H); 3.4 (3H); 3.6 (2H); 3.7–4.2 (4H); 4.7 (1H); 5.1 (1H); 6.8 (2H); 7.4 (2H); $[\alpha]_D^{20} = +19.3°$ (c=1, $CH_2Cl_2$); oil.
3-[4-(3(R)-acetoxypentyl)phenyl]-5(R)-methoxymethyl-2-oxazolidinone (code number MD 230323):
$^1$H NMR (CDCl$_3$) $\delta$ ppm: 1.2 (3H); 1.6 (4H); 2 (3H); 2.6 (2H); 3.4 (3H); 3.6 (2H); 3.7–4.2 (2H); 4.8 (2H); 7.1 (2H); 7.4 (2H);
IR (microcell) $\nu$ cm$^{-1}$): 1760–1730; $[\alpha]_D^{20} = -31.5°$ (c=1, $CH_2Cl_2$).

Step 2: 3-[4-(3(S)-hydroxybutoxy)phenyl]-5(S)-methoxymethyl-2-oxazolidinone (code number MD 370121)

6.1 g of the compound having code number MD 370162 are dissolved in 63 cm$^3$ of $CH_3OH$, 18 ml of 2N sodium hydroxide are added within 20 min. and the mixture is left under stirring for 3 hours, and then, the reaction medium is diluted with methylene chloride which is washed with water, dried over $Na_2SO_4$ and concentrated. The aimed product is obtained with a 83% yield;
m.p.=76° C.; $[\alpha]_D^{20} = +50.4°$ (c=1, $CH_2Cl_2$).

In the same manner, but starting from the compound having code number MD 370161, there is obtained with a 80% yield:
4-[4-(3(S)-hydroxybutoxy)phenyl]-5(R)-methoxymethyl-2-oxazolidinone derivative (code number MD 370122)
$[\alpha]_D^{20} = -33.4°$ (c=1, $CH_2Cl_2$);
$^1$H NMR (CDCl$_3$) $\delta$ ppm: 1.2 (3H); 1.8 (2H); 2.2 (1 exch. H); 3.4 (3H); 3.6 (2H); 3.7–4.2 (5H); 4.7 (1H); 6.8 (2H); 7.4 (2H);
$^{13}$C NMR (CDCl$_3$) $\delta$ ppm: Cq: 155.6; 154.9; 131.6; CH: 120.2; 115, 71.3; 65.6 CH$_2$: 72.7; 65.9; 47.6; 38.2; CH$_3$: 59.6; 23.6.
IR (KBr, $\nu$ cm$^{-1}$): 3380–3400, 1755, 1730.
m.p.: 49° C.

Likewise, starting from compound MD 230323, there is obtained the 3-[4-(4(R)-hydroxypentyl)phenyl]- 5(R)-methoxymethyl-2-oxazolidinone derivative (code number MD 230238):

m.p.: 53° C., $[\alpha]_D^{20}$: −35.9° (c=1, $CH_2Cl_2$)
IR (KBr) $\nu$ cm$^{-1}$: 3400, 1740.

EXAMPLE 4

3-[4-(3(S)-hydroxybutoxy)phenyl]-5(R)-methoxymethyl-2-oxazolidinone (code number MD 370122)

Step 1: (S)ethyl 2-(1-ethoxyethoxy)butanoate (code number MD 370365).

To a solution of 15 g (0.113 mol) of (S)ethyl 2-hydroxybutanoate in 150 ml of $CH_2Cl_2$ cooled at 0° C. under argon, are added 16.3 g (0.227 mol) of ethylvinylether, and then 3 drops of $POCl_3$. The temperature is let rise to 25° C. and a solution of sodium bicarbonate is added. The organic solution is dried over $Na_2SO_4$ and concentrated. The product is purified by flash chromatography (silica, eluent: petroleum ether: 90; isopropyl ether: 10) with a 48% yield.

$[\alpha]_D^{20}$ = +10.3° (c=1, $CHCl_3$)

Step 2: 3(S)-(1-ethoxyethoxy)-1-butanol (code number 370366)

To a suspension of 1.36 g (0.0625 mol) of lithium borohydride in 50 ml of DME (dimethoxyethane), are added 25.48 g (0.125 mol) of compound having code number 370365 dissolved in DME. The reaction medium is heated under reflux. After 1 hour, 0.5 equivalent of $LiBH_4$ is added, and the mixture is left under stirring overnight. After adding water, the reaction medium is extracted with $CH_2Cl_2$. The organic phase is washed with NaCl saturated water, the aimed product is isolated with a 58% yield after flash chromatography (silica, ethyl acetate: 50; heptane: 50):

$[\alpha]_D^{20}$ = +57.6° (c=1 $CHCl_3$).

Step 3: 4-[3(S)-(1-ethoxyethoxy)butoxy]phenyl-5(R)-methoxymethyl-2-oxazolidinone (code number MD 370367).

To a solution of 6.6 g of compound MD 370366 (0.04 mol) in 70 ml of THF, are added at 0° C. 4.5 g (0.044 mol) of triethylamine and 5.1 g (0.044 mol) of mesyl chloride. The mixture is left under stirring for 10 min. and the reaction medium is poured on water. The organic phase is extracted with isopropyl ether. The ethereal phase is washed with salted water, and then dried over $Na_2SO_4$ and concentrated. The resulting product is used without further purification for the subsequent step.

To a solution of 7.6 g (0.034 mol) of compound MD 200405 (Ex. 2, Step 3) in 20 ml of dimethylformamide (DMF) and 200 ml of butanone, are added 11.7 g (0.085 mol) of $K_2CO_3$, a small amount of KI and 9 g (0.0374 mol) of the previously obtained compound. The reaction medium is heated under reflux for 6 hours, and then poured on a 0.5N sodium hydroxide solution.

After extracting with ethyl acetate, the organic phase is washed with salt saturated water, dried over $Na_2SO_4$ and concentrated. The product is obtained with a 92% yield after flash chromatography (silica, eluent: Heptane: 50; AcOEt: 50). $[\alpha]_D^{20}$: −12.1° (c=1, $CH_2Cl_2$)

Step 4: 3-[4-(3(S)-hydroxybutoxy)phenyl]-5(R)-methoxymethyl-2-oxazolidinone (code number MD 370122)

To a solution of 236 g (0.642 mol) of compound MD 370367 in 250 ml of THF, are added at room temprature 250 ml of 1N HCl. After 15 min. of stirring, 10.8N ammonia is added until pH: 10. The aqueous phase is extracted with ethyl acetate and the organic solution is washed with salted water. After concentration, the resulting product is purified by flash chromatography (eluent: ethyl acetate: 33; isopropyl ether: 66). The product has the same characteristics as those obtained in Example 3.

EXAMPLE 4a:

Racemic mixture of diasteroisomers of 3-acetoxy-4-butoxy-3-phenyl-5-methoxymethyl-2-oxazolidinone (code number MD 370057).

Method 1

100 mg of compound MD 370047 (described in Example 1) and 29 mg of acetyl chloride in the presence of 51 mg of triethylamine are left under stirring in 1 ml of $CH_2Cl_2$, and then $CH_2Cl_2$ is added, the organic solution is washed with water, dried, concentrated. The aimed product is purified by flash chromatography (silica, eluent: Heptane: 40; Ethyl acetate: 60) with a 33% yield.

$^1H$ NMR ($CDCl_3$) $\delta$ ppm: 1.3 (3H); 2 (5H); 3.4 (3H); 3.6 (2H); 3.7–4.2 (4H); 4.7 (1H); 5.1 (1H); 6.8 (2H); 7.4 (2H);

IR (microcell) $\nu$ cm$^{-1}$: 1740, 1760.

Method 2

To a solution cooled at 0° C. of 6 g (0.02 mol) of compound MD 370047 in 8.2 ml of pyridine, are added 2.4 ml of acetic anhydride and 3.5 ml of triethylamine. The mixture is left under stirring for 12 hours at room temperature. Then, the reaction medium is diluted with $CH_2Cl_2$. The organic solution is washed with water until neutral pH, dried over $Na_2SO_4$ and concentrated. The aimed product is purified as previously described with a 83% yield.

EXAMPLE 4b:

3-[4-(3(S)-methoxybutoxy)phenyl]-5(R)-methoxymethyl-2-oxazolidinone (code number: MD 370375).

To a solution of 6 g (0.02 mol) of compound MD 370122 in 60 ml of DMF, is added 1.07 g of 50% NaH, and the mixture is left at 40° C. for 30 min., and then 1.8 ml of methyl iodide (0.03 mol) is added. After 1 hour of stirring, the reaction medium is poured on a mixture $H_2OCH_2Cl_2$. The organic phase is dried over $Na_2SO_4$ and concentrated. The product is obtained with a 63% yield after flash chromatography (silica, eluent: Ethyl acetate: 70; Heptane: 30):

$^1H$ NMR ($CDCl_3$) $\delta$ ppm: 1.2 (3H); 1.9 (2H); 3.3 (3H); 3.4 (3H); 3.6 (2H); 3.7–4.2 (4H); 4.7 (1H); 6.9 (2H); 7.4 (2H);

IR (microcell) $\nu$ cm$^{-1}$: 1740–1760;

$[\alpha]_D^{20}$: −18.7° (c=1, $CH_2Cl_2$); oil

In the same manner, there was obtained:

3-[4-(3(R)-methoxybutoxy)phenyl]-5(R)-methoxymethyl-2-oxazolidinone (code number MD 370374):

m.p. = 54° C.;
$[\alpha]_D^{20}$: −58.1° (c=1, $CH_2Cl_2$);
$^1H$ NMR ($\delta$ ppm) $CDCl_3$: 1.2 (3H); 1.9 (2H); 3.3 (3H); 3.4 (3H); 3.5–4.2 (7H); 4.7 (2H); 6.85 (2H).

EXAMPLE 5

Mixture of racemic diasteroisomers of 3-[4-(3-hydroxybutoxy)phenyl]-5-hydroxymethyl-2-oxazolidinone (code number MD 370210):

To a solution of 7.8 g of 3-[(4-hydroxy)phenyl]-5-hydroxymethyl-2-oxazolidinone (MD 760172) in 75 ml of methylethylketone, are added 10.2 g (0.074 mol) of $K_2CO_3$, 0.1 g of KI and 10.84 g (0.044 mol) of 3-hydroxy-1-butanol tosylate, the mixture is heated under reflux for 12 hours. After filtration, the reaction medium is concentrated and the product is obtained after chromatography (silica, eluent: $CH_2Cl_2$: 92; $CH_3OH$: 8) with a 52% yield, m.p.: 95° C.;

$^1$H NMR (DMSOd$_6$) δ ppm: 1.2 (3H); 1.75 (2H); 3.5–4.2 (7H); 4.5 (1 exch. H); 4.6 (1H); 5.2 (1 exch. H); 6.9 (2H); 7.4 (2H).

In the same manner, there were obtained from the corresponding reagents:

3-[4-(3(R)-hydroxybutoxy)phenyl]-5(R)-hydroxymethyl-2-oxazolidinone (code number MD 370327):

$^1$H NMR (DMSOd$_6$) δ ppm: 1.1 (2H); 1.7 (2H); 3.5–4.2 (2H); 4.4 (1 exch. H); 4.6 (1H); 5.2 (1H); 6.9 (2H); 7.4 (2H).

IR (KBr) ν cm$^{-1}$: 3520, 3460;

$[α]_D^{20}$: −66.6° (c=1, ethanol);

m.p.=125° C.

3-[4-(3(S)-hydroxybutoxy)phenyl]-5(R)-hydroxymethyl-2-oxazolidinone (code number MD 370308):

$^1$H NMR (DMSOd$_6$) δ ppm: 1.1 (2H); 1.7 (2H); 3.5–4.2 (7H); 4.5 (1 exch. H); 4.6 (1H); 5.2 (1 exch. H); 6.9 (2H); 7.4 (2H).

IR (KBr) ν cm$^{-1}$: 3530, 3470, 1730.

$[α]_D^{20}$: −26.2° (c=1, $CH_3OH$); m.p.=111° C.

3-[4-(3-benzyloxybutoxy)phenyl]-5-hydroxymethyl-2-oxazolidinone (code number MD 370380):

$^1$H NMR (DMSOd$_6$) δ ppm: 1.2 (3H); 2 (2H); 3.4–4.3 (8H of which 1 exch.); 4.4–4.8 (3H); 6.8 (2H); 7.3 (5H); 7.4 (2H).

IR (KBr) ν cm$^{-1}$: 3460, 1715.

m.p.=78° C.

3-[4-(3-benzyloxybutoxy)phenyl]-5(R)-hydroxymethyl-2-oxazolidinone (code number MD 370373):

$^1$H NMR (CDCl$_3$) δ ppm: 1.2 (3H); 2 (2H); 3.5–4.2 (8H of which 1 exch.); 4.4–4.8 (3H); 6.8 (2H); 7.3 (5H); 7.4 (2H).

IR (KBr) ν cm$^{-1}$: 3460, 1715.

$[α]_D^{20}$: −33.2° (c=1, $CH_2Cl_2$).

m.p.=72° C.

Mixture of diastereoisomers of 3-[4-(4,4,4-trifluoro-3-hydroxybutoxy)phenyl]-5-hydroxymethyl-2-oxazolidinone (code number MD 370262):

m.p.=130° C., $^1$H NMR (DMSOd$_6$) δ ppm: 2 (2H); 3.5–4.2 (7H); 4.7 (1H); 5.2 (1 exch. H); 6.4 (1 exch. H; 6.9 (2H); 7.5 (2H);

IR (KBr) ν cm$^{-1}$: 3300, 1720.

3-[4-(4,4,4-trifluoro-3(R)-hydroxybutoxy)phenyl]-5(R)-hydroxymethyl-2-oxazolidinone (code number MD 230100):

$^1$H NMR (DMSOd$_6$) δ ppm: 2(2H); 3.6–4.4 (7H); 4.7 (1H); 5.1 (1 exch. H); 6.3 (1 exch. H); 7 (2H); 7.5 (2H).

IR (KBr) ν cm$^{-1}$: 3400, 3300, 1725.

$[α]_D^{20}$: −2.5° (c=1, $CH_3OH$); m.p=117° C.

EXAMPLE 6

3-[4-(4-hydroxypentoxy)phenyl]-5(R)-methoxymethyl-2-oxazolidinone (code number MD 370509).

To a solution of 10.9 g (0.035 mol) of compound MD 370507 (Ex. 9) in 150 ml of ethanol heated at 45° C.–50° C., is added by small portions 1.347 g (0.035 mol) of sodium borohydride. And then the reaction medium is concentrated and the residue is taken up in 200 ml of water. After extracting with $CH_2Cl_2$, the organic phase is dried over $Na_2SO_4$, concentrated. The product is obtained with a 81% yield after crystallisation from a mixture of ethyl acetate-hexane.

m.p.:56° C.;

$[α]_D^{20}$: −39.8° (c=1, $CH_2Cl_2$);

$^1$H NMR (CDCl$_3$) δ ppm: 1.2 (3H); 1.7 (4H); 2.2 (1 exch. H); 3.4 (3H); 3.6 (2H); 3.7–4.2 (5H); 4.7 (1H); 6.9 (2H); 7.4 (2H).

IR (KBr) ν cm$^{-1}$: 3350, 1745, 1730.

In the same manner, there were obtained from the corresponding starting materials:

3-[4-(3-hydroxybutoxy)phenyl]-5(R)-methoxymethyl-2-oxazolidinone (code number MD 370284)

$^1$H NMR (CDCl$_3$) δ ppm: 1.2 (3H); 1.8 (2H); 2.6 (1 exch. H); 3.4 (3H); 3.6 (2H); 3.7–4.2 (5H); 4.7 (1H); 6.8 (2H); 7.4 (2H).

IR (KBr) ν cm$^{-1}$: 3400, 1745, 1730;

$[α]_D^{20}$: −41.5° (c=1, $CH_2Cl_2$)

3-[4-(1-hydroxy-2-cyclopentylmethoxy)phenyl]-5(R)-methoxymethyl-2-oxazolidinone (code number MD 230201)

m.p.: 71° C.;

$[α]_D^{20}$: −40.3° (c=1, $CH_2Cl_2$);

IR (KBr) ν cm$^{-1}$: 3400–3300, 1755, 1730;

$^1$H NMR (CDCl$_3$) δ ppm: 1.1–2.5 (7H); 2.8 (1 exch. H; 3.4 (3H); 3.6 (2H) 4 (5H); 4.7 (1H); 6.9 (2H); 7.4 (2H).

EXAMPLE 7

3-[4-(4,4,4-trifluoro-3(R)-hydroxybutoxy)phenyl]-5(R)-methoxymethyl-2-oxazolidinone (code number MD 370503)

Step 1: Ethyl 4,4,4-trifluoro-3-hydroxybutanoate (code number MD 370270).

To a suspension of 91.2 g (2.4 mol) of sodium borohydride in 6 l of $CH_2Cl_2$ cooled at +2° C., are dropwise added 1473 g of ethyl 4,4,4-trifluoroacetoacetate while keeping temperature between +4° and +7° C. After the introduction, 100 ml of absolute ethanol are added while keeping temperature at +3° C. The reaction medium is washed with bicarbonated water. The organic phase is concentrated and the product is distilled at 78° C. under 10 mm Hg.

m.p.=16° C.

Step 2: 4,4,4-trifluoro-3-hydroxybutanoic acid (code number MD 230096).

To 3 l of absolute ethanol, are added 228 g of NaOH. The resulting sodium hydroxide solution in ethanol is added to the solution of compound MD 370270 (1060 g, 5.7 mol) in 1 l of absolute ethanol while keeping temperature at 20° C. After 3 hours of contact, the sodium salt is filtered and dried.

To a solution of 4.5 l of ethyl acetate, 910 ml of water and 450 ml of 12N HCl, is added the previously obtained sodium salt, and the mixture is left under stirring until obtaining a solution.

The reaction medium is extracted with ethyl acetate and concentrated.

The product is crystallized from heptane with a 85.9% yield: m.p.=78° C.

Step 3: 4,4,4-trifluoro-3(R)-hydroxybutanoic acid (code number MD 230097).

To a solution of 7.8 l of ethanol containing 766.7 g (4.85 mol) of racemic 4,4,4-trifluoro-3-hydroxybutanoic acid, are added 575.7 g of (S) α-methylbenzylamine. The reaction medium is heated until dissolution. After one night at 20° C., the precipitate is filtered and dried. After recrystallizations from ethanol, there is obtained a constant rotatory power $[α]_D^{20}$ −8.8° and a constant melting point: m.p.=196° C. To a mixture of 200 ml of water, 150 ml of 36% HCl and 1.2 l of ethyl ether, are added 434 g of the previously obtained product. The aqueous phase is extracted with ethyl ether and the organic phases are dried over $Na_2SO_4$ and concentrated. The product is purified by distillation under 4 mm Hg at 110° C.; m.p.=40° C.; $[\alpha]_D^{20}$: +18.8° (c=1, pyridine); Yield=66%

| Elemental analysis: | calc. % | C: 30.39; | H: 3.19. |
|---|---|---|---|
| | found % | C: 30.69; | H: 3.21. |

The 4,4,4-trifluoro-3-hydroxybutanoic acid of configuration (S) was likewise obtained but using (R) α-methyl-benzylamine.

m.p.=40° C.; $[\alpha]_D^{20}$: −18.8° (c=1, pyridine).

Step 4: 4,4,4-trifluorobutane-1,3(R)-diol (code number MD 230098).

To a suspension of 75.8 g (2 mol) of sodium borohydride in 1.2 l of THF cooled at −2° C., are added 243 g (1.537 mol) of compound MD 230097 dissolved in 300 ml of THF over 55 min. And then 320 ml of $BF_3$ etherate are added within 40 min. while keeping temperature between 2° C. and 10° C. After 35 min. of stirring, water is dropwise added within 35 min., and the temperature is let rise to 21° C.

After one night of stirring, the reaction medium is concentrated and the residue, filtered. To the cooled oil, are added 600 ml of 10% sodium hydroxide. The aqueous phase is extracted with ethyl ether, and then with ethyl acetate. The organic phases are concentrated and the residue is taken up in ethyl ether. The solution is acidified with aqueous HCl to bring the pH to 1–2. After filtration and concentration, the product is purified by flash chromatography (silica, eluent: Heptane: 70; Ethyl acetate: 30);

b.p.$_4$=78° C.; $[\alpha]_D^{20}$=+28.9° (c=1, $CHCl_3$).

By the same process, there is obtained the (S) optical antipode $[\alpha]_D^{20}$=−28.9° (c=1, $CHCl_3$).

Step 5: 4,4,4-trifluoro-1-tosyloxy-3(R)-butanol (code number MD 230099).

To a solution of 120 g (0.833 mol) of compound MD 230098 in 335 ml of pyridine, are added 0.12 g of 4-dimethylaminopyridine and a solution of 198.4 g (1.041 mol) of tosyl chloride in 200 ml of $CH_2Cl_2$. After 1 hour 20 min. of stirring, 1.2 l of $CH_2Cl_2$ and 1.5 l of water are added. The organic phase is concentrated and the product is purified by chromatography (silica, eluent: Heptane: 80; Ethyl acetate: 20) and is obtained with a 78% yield. It is used directly for the subsequent step.

Step 6: 3-[4-(4,4,4-trifluoro-3(R)-hydroxybutoxy)-phenyl]5(R)-methoxymethyl-2-oxazolidinone (code number MD 370503).

To a solution of 192.1 g (0.644 mol) of compound MD 200405 (Ex. 2, Step 3) in 400 ml of DMF, are added 161.5 g of $K_2CO_3$ and the mixture is heated at 90° C., and then the suspension of the compound MD 230099 in 200 ml of DMF. After 1 hour, the reaction medium is cooled and 1.2 l of toluene by liter of water is added.

After extracting the aqueous phase with toluene, the organic phases are concentrated to dryness. The product is recrystrallized from a mixture ethanol-isopropyl ether. Yield: 60.8%; m.p.: 101° C.;

$^1$H NMR ($CDCl_3$) δ ppm: 2.05 (2H); 3.4 (3H); 3.6 (2H); 3.6–4.4 (6H of which 1 exch.); 4.6 (1H); 6.8 (2H); 7.3 (2H).

$^{13}$C NMR (DMSO$_{d6}$):

Cq: 154.6; 154.4; 125.9 ($^1$JCF: 289.6 Hz); 131.8;
CH: 119.8; 114.8; 71.3; 65.4 ($^2$JCF 30.4 Hz);
$CH_2$: 72.5; 63.2; 46.6; 29.4;
$CH_3$: 58.7;
IR (KBr) ν cm$^{-1}$: 3400, 1730, 1720;
$[\alpha]_D^{20}$: −11.5° (c=1, $CH_2Cl_2$)

In the same manner, but starting from 4,4,4-trifluoro-1-tosyloxy-3(S)-butanol and from compound MD 200405, there was obtained 3-[4-(4,4,4-trifluoro-3(S)-hydroxybutoxy)phenyl]-5(R)-methoxymethyl-2-oxazolidinone (code number MD 370504).

m.p.: 121° C.; $[\alpha]_D^{20}$: −59.7° (c=1, $CH_2Cl_2$)

$^1$H NMR ($CDCl_3$) δ ppm: 2.1 (2H); 3.4 (4H of which 1 exch.); 3.6 (2H); 3.7–4.4 (5H); 4.7 (1H); 6.8 (2H); 7.4 (2H);

IR (KBr) ν cm$^{-1}$: 3420, 1735.

From the racemic 4,4,4-trifluoro-1-tosyloxy-3-butanol compound (code number MD 370272) and from compound MD 200405, there was obtained in the same conditions the mixture of diastereoisomers 3-[4-(4,4,4-trifluoro-3-hydroxybutoxy)phenyl]-5(R)-methoxymethyl-2-oxazolidinone (code number MD 230016).

$^1$H NMR ($CDCl_3$+DMSO) δ ppm: 1.8–2.3 (2H); 3.4 (3H); 3.6 (2H); 3.8–4.4 (5H); 4.7 (1H); 5.3 (1 exch. H); 6.9 (2H); 7.4 (2H);

IR (KBr) ν cm$^{-1}$: 3400, 1755, 1735.

m.p.: 103° C; $[\alpha]_D^{20}$: −35.2° (c=1, $CH_2Cl_2$)

In the same manner but starting from the corresponding materials, there were obtained:

3-[4-(4,4,4-trifluoro-3(S)-hydroxybutoxy)phenyl]-5(S)-methoxymethyl-2-oxazolidinone (code number MD 230154):

$[\alpha]_D^{20}$: +9.9° (c=1, $CH_2Cl_2$)
m.p.=100° C.

3-[4-(4,4,4-trifluoro-3(R)-hydroxybutoxy)phenyl]-5(S)-methoxymethyl-2-oxazolidinone (code number MD 230151): $[\alpha]_D^{20}$: +59.2° (c=1, $CH_2Cl_2$)
m.p.=123° C.

3-[4-(4,4,4-trifluoro-3(R)-hydroxybutoxy)phenyl]-5(R)-ethoxymethoxy-2-oxazolidinone (code number MD 230197):

m.p.: 91° C.; $[\alpha]_D^{20}$: −11.4° (c=1 $CH_3OH$);
IR (KBr) ν cm$^{-1}$: 3400, 1750, 1735, $^1$H NMR ($CDCl_3$) δ ppm: 1.1 (3H); 3.3–4.4 (9H); 4.7 (1H); 6.3 (1 exch. H); 6.9 (2H); 7.4 (2H).

EXAMPLE 8

3-[4-[2-(2-methyl-1,3-dioxolane-2-yl)ethoxy]phenyl]-5(R)-methoxymethyl-2-oxazolidinone (code number MD 370296)

To a solution of 50 ml of DMF, are added 3 g (0.076 mol) of 60% NaH and, within 15 min., 16 g (0.076 mol) of compound MD 200405 (Ex. 2 - Step 3) dissolved in 75 ml of DMF. Then, while keeping temperature at 20° C., 0.0836 mol of 2-(2-mesyloxyethyl)-2-methyldioxolane dissolved in 25 ml of DMF. The reaction medium is left at room temperature for 24 hours and poured on iced water. The aqueous phase is extracted with $CH_2Cl_2$ and the organic phase is dried over magnesium sulphate. The product is obtained after purification on silica column (eluent : Heptane : 40 ; Ethyl acetate : 60) with a 44% yield;

m.p.=48° C.; $[\alpha]_D^{20}$=−32.8° (c=1, $CH_2Cl_2$);

$^1$H NMR (CDCl$_3$) δ ppm: 1.4 (3H) 2.2 (2H) 3.4 (3H) 3.6 (2H) 3.9 (4H); 3.7–4.3 (4H); 4.7 (1H); 6.8 (2H); 7.4 (2H);

IR (KBr) ν cm$^{-1}$: 1740.

$^{13}$C NMR:
Cq: 155.6; 154.4; 131.5; 108.7;
CH: 120.2; 114.9; 712;
CH$_2$: 72.7; 64.6; 64.3; 47.5; 38.2;
CH$_3$: 59.6; 24.4.

In the same manner, there were obtained

3-[4-[3-(2-methyl-1,3-dioxolane-2-yl)propoxy]phenyl]-5(R)-methoxymethyl-2-oxazolidinone (code number MD 370506):

$^1$H NMR (CDCl$_3$) δ ppm: 1.35 (3H); 1.8 (4H); 3.4 (3H); 3.6 (2H); 3.7–4.2 (4H); 3.9 (4H); 4.7 (1H); 6.8 (2H); 7.4 (2H);

IR (KBr) ν cm$^{-1}$: 1750.

m.p.=67° C.;

3-[4-[2-(2-methyl-1,3-dioxolane-2-yl)ethoxy]phenyl]-5(R)-hydroxymethyl-2-oxazolidinone (code number MD 230046):

$^1$H NMR (CDCl$_3$) δ ppm: 1.4 (3H); 2.15 (2H); 3 (1 exch. H); 3.9 (4H); 3.6–4.2 (6H); 4.6 (1H); 6.2 (2H); 7.4 (2H);

IR (KBr) ν cm$^{-1}$: 3480, 1710.

$[α]_D^{20}$ = −40.2° (c=1, CH$_2$Cl$_2$);

m.p.=132° C.

yield=96%;

3-[4-(1,3-dioxaspiro[4,4]nonane[1,4]-6-yl-methoxy)-phenyl]-5(R)-methoxymethyl-2-oxazolidinone (code number MD 230204):

$[α]_D^{20}$ = −44.8° (c=1 CH$_3$OH);

$^1$H NMR (CDCl$_3$) δ ppm: 1.4–2.6 (7H); 3.4 (3H); 3.6 (2H); 3.8–4.2 (8H); 4.7 (1H); 6.9 (2H); 7.4 (2H);

Oil.

EXAMPLE 9

3-[4-(3-oxobutoxy)phenyl]-5(R)-methoxymethyl-2-oxazolidinone (code number MD 370268)

To a solution of 294 g (0.871 mol) of compound MD 370296 (Example 8) in 2.5 l of acetone, are added 600 g of (FeCl$_3$, 6H$_2$O, SiO$_2$)$_n$ within 10 min. After 4 hours of stirring, the reaction medium is filtered and dried over Na$_2$SO$_4$ and concentrated. The product is obtained with a 74.1% yield.

m.p.=49° C.; $[α]_D^{20}$ = −42.6° (c=1, CH$_2$Cl$_2$);

$^1$H NMR (CDCl$_3$) δ ppm: 2.2 (3H); 2.85 (2H); 3.4 (3H); 3.6 (2H); 3.8–4.4 (4H); 4.7 (1H); 6.8 (2H); 7.4 (2H);

IR (KBr) ν cm$^{-1}$: 1750, 1710.

By this process, there were also obtained:

3-[4-(4-oxopentoxy)phenyl]-5(R)-methoxymethyl-2-oxazolidinone (code number MD 370507)

$^1$H NMR (CDCl$_3$) δ ppm: 2 (2H); 2.15 (3H); 2.6 (2H); 3.4 (3H); 3.6 (2H); 3.9 (4H); 4.65 (1H); 6.8 (2H); 7.4 (2H);

IR (KBr) ν cm$^{-1}$: 1760, 1710;

$[α]_D^{20}$ = −40.3° (c=1, CH$_2$Cl$_2$);

m.p.=70° C.

3-[4-(3-oxobutoxy)phenyl]-5(R)-hydroxymethyl-2-oxazolidinone (code number MD 230047)

$^1$H NMR (CDCl$_3$) δ ppm: 2.2 (3H); 2.9 (2H); 3.3–4.3 (4H); 4.2 (2H); 4.7 (1H); 5.2 (1 exch. H) 6.9 (2H); 7.5 (2H);

IR (KBr) ν cm$^{-1}$: 3450, 1720;

$[α]_D^{20}$ = −49.4° (c=1, CH$_3$OH);

m.p.=126° C.

3-[4-(1-oxo-2-cyclopentylmethoxy)phenyl]-5(R)-methoxymethyl-2-oxazolidinone (code number MD 230200)

m.p.: 70° C.; $[α]_D^{20}$: −51.2° (c=1, CH$_3$OH);

$^1$H NMR (CDCl$_3$) δ ppm: 1.8–2.1 (7H); 3.4 (3H); 3.6 (2H); 3.8–4.2 (4H); 4.7 (1H); 6.9 (2H); 7.4 (2H).

EXAMPLE 10

3-[4-(3-oxo-2,2-dimethylbutoxy)phenyl]-5(R)-hydroxymethyl-2-oxazolidinone (code number MD 230109)

Step 1: 2,2-Dimethyl-2-(2-methyl 1,3 dioxolane-2-yl)ethanol (code number MD 230103)

A solution of 35 g (0.073 mol) of 2,2-dimethyl-2-(2-methyl-1,3-dioxolane-2-yl) acetic acid ethyl ester in 50 ml of THF is added at 0° C. to a suspension of 7.23 g (0.19 mol) of LiAlH$_4$ in 300 ml of THF within 15 min. Then the reaction medium is hydrolyzed with 20 ml of water. After filtration and concentration, the product is obtained with a 92% yield.

IR (KBr) ν cm$^{-1}$: 3450, 2980, 2880;

$^1$H NMR (CDCl$_3$): 1 (6H); 1.2 (3H); 3.5 (2H); 4 (4H).

Step 2: 2-methyl-2-[2-(4-nitrophenoxy -1,1-dimethylethyl]-1,3-dioxolane (code number MD 230105)

To a solution of 1.6 g (0.01 mol) of compound MD 230103 in 13 ml of DMF, is added 0.48 g (0.01 mol) of 50% NaH. After 15 min. of stirring, a solution of 1.32 g (0.0084 mol) of parachloronitrobenzene is added and agitated at room temperature for 30 min.

The reaction medium is poured on water and extracted with isopropyl ether. The organic phases are washed with NaCl saturated water, dried over Na$_2$SO$_4$ and concentrated. The product is purified by flash chromatography (silica, eluent: heptane: 80; ethyl acetate: 20). Yield: 68%; oil;

$^1$H NMR (CDCl$_3$) δ ppm: 1.1 (6H); 1.3 (3H); 4 (6H); 6.9 (2H); 8.1 (1H).

Step 3: 2-methyl-2-[2-(4-aminophenoxy)-1,1-dimethylethyl]-1,3-dioxolane (code number MD 230106)

To a solution of 18.4 g (65.4×10$^{-3}$ mol) of compound 230105 in 180 ml of ethanol in the presence of 50% humidified 10% Pd/C, a hydrogen stream is passed through under normal pressure for 3 h 30. After filtration and concentration, the product is purified by flash chromatography (silica, eluent: ethyl acetate: 30; heptane: 70).

$^1$H NMR (CDCl$_3$) δ ppm: 1.05 (6H); 1.3 (3H); 3.3 (2 exch. H); 3.7 (2H); 3.9 (4H); 6.7 (4H).

IR (microcell) ν cm$^{-1}$: 3460, 3450.

Step 4: N-[4-[2-(2-methyl-1,3-dioxolane-2-yl)-1,1-dimethylethoxy]phenyl]-1,4-dioxaspiro[4,5]decane -2-methanamine (R) (code number MD 230107)

8.8 g (0.035 mol) of compound MD 230106, 12.6 g (0.036 mol) of 1,4-dioxaspiro[4,5]decane-2-methanol (S) mesylate and 5.4 g (0.054 mol) of triethylamine are heated in a bomb at 130° C.–140° C. for 2 h. After cooling, the reaction mixture is taken up in ethyl acetate. The organic phase is washed with NaCl saturated water, dried and concentrated. The product is obtained after chromatography (silica, eluent: heptane 80-ethyl acetate 20). Yield: 63%.

$^1$H NMR (CDCl$_3$) δ ppm: 1.1 (6H); 1.35 (3H); 1.6 (10H); 3.2 (2H); 3.6–4.5 (10 H of which 1 exch.); 6.65 (4H).

IR (microcell) ν cm$^{-1}$: 3400.

$[α]_D^{20}$ = −1.2° (c=2, MeOH).

Step 5: 3-[4-(3-oxo-2,2-dimethylbutoxy)phenyl]aminopropane-1,2-diol (R) (code number MD 230108)

To a solution of 0.7 g (1.7 10⁻¹mol) of compound MD 230107 in 3.5 ml of THF, are dropwise added 3.5 ml of 6N hydrochloric acid. After 1 h, the reaction medium is poured on water and extracted with ethyl acetate. The organic phase is washed with water, dried over $Na_2SO_4$ and concentrated. 80% yield.

IR (microcell) $\nu$ cm⁻¹: 3400, 1710.

Step 6: 3-[4-(3-oxo-2,2-dimethylbutoxy)phenyl]-5(R)-hydroxymethyl-2-oxazolidinone (code number MD 230109)

This compound was obtained according to the procedure of Step 2 a) of Example 2:

m.p.=109° C.; $[\alpha]_D^{20}=-44.4°$ (c=1, MeOH);

¹H NMR (CDCl₃) $\delta$ ppm: 1.25 (6H); 2.2 (3H); 3.9 (6H); 4.7 (1H); 6.9 (2H); 7.4 (2H).

IR (KBr) $\nu$ cm⁻¹: 3450, 1745–1725.

EXAMPLE 11

3-[4-(3-oxo-2,2-dimethylbutoxy)phenyl]-5(R)-methoxymethyl-2-oxazolidinone (code number MD 230073)

To a suspension of 2.9 g (0.009 mol) of compound MD 230109 in 40 ml of toluene, are added 3.8 g of 50% sodium hydroxide, 0.3 g of tetrabutylammonium bromide and 3.6 g (0.0283 mol) of methyl sulphate. After 10 min. of stirring, the reaction medium is poured on water. The organic phase is washed, dried over $Na_2SO_4$ and concentrated and the product is obtained after chromatography (silica, eluent: ethyl acetate: 50; heptane: 50);

m.p.: 75° C.; $[\alpha]_D^{20}=-52°$ (c=1 MeOH);

¹H NMR (CDCl₃) $\delta$ ppm: 1.25 (6H); 2.2 (3H); 3.6 (2H); 3.7–4.2 (2H); 3.9 (2H); 4.65 (1H); 6.8 (2H); 7.4 (2H);

¹³C NMR (CDCl₃) $\delta$ ppm:
Cq: 211.9; 155.8; 154.9; 132; 48.4;
CH: 120.3; 115.1; 71.3;
CH₂: 74.9; 72.8; 47.8;
CH₃: 25.8; 22;

IR (KBr) $\nu$ cm⁻¹: 1735, 1715.

EXAMPLE 12

3-[4-(4-oxopentyl)phenyl]-5(R)-hydroxymethyl-2-oxazolidinone (code number MD 230116)

Step 1: 2-(p-nitrocinnamyl)-2-methyl-1,3-dioxolane (code number MD 230111)

To 62.8 mmol of LDA in 226.4 ml of THF, is added dropwise at 0° C. a solution of 28.8 g (62.2 mmol) of (2-methyl-dioxolane-2-yl-2-ethyl)triphenylphosphonium bromide in 60 ml of DMSO. After 1 h at 0° C., 7.8 g (51.6 mmol) of p-nitrobenzaldehyde dissolved in 40 ml of THF are added. The reaction medium is hydrolyzed with a NH₄Cl saturated solution and is extracted with ethyl ether. The organic phase is dried over $Na_2SO_4$ and concentrated. After purification by flash chromatography (silica, eluent: heptane: 70; ethyl acetate: 30), the product is obtained with a 48% yield.

¹H NMR (CDCl₃) $\delta$ ppm: 1.3 (3H); 2.6 (2H) 4 (4H) 5.7–6.5 (2H); 7.4 (2H); 8.1 (2H).

Step 2: 2-(4-aminocinnamyl)-2-methyl-1,3-dioxolane (code number MD 230112)

To a solution of 8 g (32 mmol) of compound MD 30111 in 100 ml of ethanol in the presence of 0.8 g of 10% Pd/C in an autoclave, a hydrogen stream is passed through under 5 atm for 4 h. After filtration, concentration, purification by flash chromatography (silica, eluent: heptane: 50; ethyl acetate: 50), the product is obtained with a 89% yield.

m.p.: <50° C.;

¹H NMR (CDCl₃) $\delta$ ppm: 1.35 (3H); 2.4–2.8 (2H); 3.6 (2 exch. H): 4 (4H) ; 5.5–6.3 (2H); 6.6 (2H); 7.2 (2H);

IR (microcell) $\nu$ cm⁻¹: 3460, 3440.

Step 3: 2-(4-aminophenylpropyl)-2-methyl-1,3-dioxolane (code number MD 230113)

A solution of 15.4 g (70.23 mmol) of compound MD 230112 in 100 ml of ethanol and 1.5 g of 10% Pd/C are charged in an autoclave; a hydrogen stream is passed through under 9 atm for 1 h at 50° C. After filtration and concentration, 15.5 g of the aimed product (liquid) are obtained.

¹H NMR (CDCl₃) $\delta$ ppm: 1.25 (3H); 1.6 (4H); 2.45 (2H); 3.5 (2 exch. H); 3.85 (4H); 6.55 (2H); 6.9 (2H).

IR (microcell, $\nu$ cm⁻¹): 3460, 3350.

Step 4: 4-[3-(2-methyl-1,3-dioxolane-2-yl)propyl]-phenyl]-1,4-dioxaspiro[4,5]decane-2-methanamine (R) (code number MD 230114)

To a mixture of 1 g (4.5 mmol) of compound MD 230113 and 1.62 g (4.97 mmol) of 1,4-dioxaspiro[4,5]-decane-2-methanol (S) tosylate, is added 0.73 g (1 ml, 7.23 mmol) of triethylamine and the mixture is heated at 140° C. for 5 h The reaction medium is taken up in water and extracted with ethyl acetate. The organic phase is washed with salted water, and then dried over $Na_2SO_4$. The product as a liquid is obtained with a 59% yield after flash chromatography (silica, eluent: heptane: 40; ethyl acetate: 60).

¹H NMR (CDCl₃) $\delta$ ppm: 1.2 (3H); 1.5 (10H); 1.6 (4H); 2.4 (3H); 3.15 (3H); 3.8 (4H); 3.6–4.5 (3H).

IR (microcell) $\nu$ cm⁻¹: 3400;

$[\alpha]_D^{20}=-2.9°$ (c=1, MeOH).

Step 5: [4-(4-oxopentyl)phenyl]aminopropane-1,2-diol (R) (code number MD 230115)

This compound was obtained according to the same procedure as that of Step 5 of Example 10

¹H NMR (CDCl₃) $\delta$ ppm: 1.8 (2H); 2 (3H); 2.4 (4H); 2.7–3.3 (3H); 3.1 (3H); 3.6 (2H); 3.3 (1H); 6.5 (2H) ; 6.9 (2H).

Step 6: 3-[4-(4-oxopentyl)phenyl]-5(R)-hydroxymethyl-2-oxazolidinone (code number MD 230116):

This compound was obtained according to the same procedure as that of the Step 6 of Example 10:

m.p.=110° C.;

$[\alpha]_D^{20}=-50.7°$ (c=1, MeOH);

¹NMR (CDCl₃) $\delta$ ppm: 1.8 (2H); 2.05 (3H); 2.2–2.7 (4H); 2.75 (1H); 3.65–4.10 (2H); 4.65 (1H); 7.1 (2H); 7.4 (2H);

IR (KBr) $\nu$ cm⁻¹: 3460, 1720.

EXAMPLE 13

3-[4-(4-oxopentyl)phenyl]-5(R)-methoxymethyl-2-oxazolidinone (code number MD 230083):

This compound was obtained from compound MD 230116 according to the procedure of Example 11:

m.p.: <50° C.;

$[\alpha]_D^{20}=-56.9°$ (c=1, MeOH);

¹H NMR (CDCl₃): 1.9 (2H); 2.1 (3H); 2.45 (4H); 3.4 (3H); 3.6 (2H); 3.9 (2H); 4.7 (1H); 7.1 (2H); 7.4 (2H);

IR (KBr) $\nu$ cm⁻¹: 1750, 1710.

EXAMPLE 14

3-[4-(4-hydroxypentyl)phenyl]-5(R)-methoxymethyl-2-oxazolidinone (code number MD 230082).

To a solution of 1.83 g (6.28 mmol) of compound MD 230083 (Example 13) in 30 ml of ethanol, is added 0.24 g (6.28 mmol) of NaBH₄. After 10 min. of reaction, water is added and the mixture is extracted with methylene chloride. The organic phase is washed with salted water and dried over $Na_2SO_4$ and concentrated. The product is obtained after flash chromatography as an oil:

$[\alpha]_D^{20} = -56.3°$ (c=1, MeOH);

$^1$H NMR (CDCl$_3$) δ ppm: 1.15 (3H); 1.55 (5H); 2.6 (2H); 3.4 (3H); 3.6 (3H); 3.9 (2H); 4.65 (1H); 7.1 (2H); 7.4 (2H);

IR (microcell) ν cm$^{-1}$: 3500-3400, 1750.

EXAMPLE 15

3-[4-(4(R)-hydroxypentyl)phenyl]-5(R)-methoxymethyl-2-oxazolidinone (code number MD 230238).

Step 1: 4-Terbutyl dimethyl silyloxy methyl-1-nitrobenzene (code number MD 230245)

To a solution of 465.4 g (3.039 mol) of paranitrobenzyl alcohol in 2.5 l of DMF, are added 310 g (4.559 mol) of imidazole, and then 504 g (3.347 mol) of terbutyl dimethylchlorosilane. After 1 h of stirring at room temperature, the reaction medium is poured on water. The aqueous phase is extracted with methylene chloride. The organic phase is dried over $Na_2SO_4$ and concentrated: oil;

$^1$NMR (CDCl$_3$) δ ppm: 0.2 (6H); 1 (9H); 4.9 (2H); 7.6 (2H); 8.2 (2H);

IR (microcell) ν cm$^{-1}$: 1520, 1340, 1030, 840.

Step 2: 4-Terbutyl dimethyl silyloxy methyl aniline (code number MD 230246)

To 772 ml of 0.1N ammonium chloride, are added 77.2 g (0.288 mol) of the previously obtained compound MD 230245 and 120.9 g of powdered iron and the mixture is heated under reflux for 2 h. After cooling, 20 ml of concentrated ammonia are added, the reaction medium is filtered and extracted with toluene. The organic phase is washed with water, dried over $Na_2SO_4$ and concentrated. b.p.$_{0.01\ mm\ Hg}$: 88°–93° C.;

| $^1$H NMR (CDCl$_3$) δ ppm: | 0.2 (6H); | 1.05 (9H); | 3.6 (2H); |
|---|---|---|---|
| | 4.8 (2H); | 6.75 (2H); | 7.2 (2H); |
| IR (microcell) ν cm$^{-1}$: | 3450, 3350. | | |

Step 3: 3-[4-(terbutyl dimethyl silyloxy methyl)-phenyl]-5(R)-methoxymethyl-2-oxazolidinone (code number MD 230247)

To a solution of 43.8 g (0.168 mol) of compound MD 370488 (Step 3 of Example17) in 200 ml of toluene, are added 130 ml of a 1.93 molar toluene solution of phosgene, and then dropwise 37.8 g (0.252 mol) of diethylaniline. After cooling, iced water is added and the organic phase is decanted and dried over $Na_2SO_4$. This solution is then added to a solution of 40 g (0.168 mol) of compound MD 230246 and of 20.5 g (0.168 mol) of dimethylaminopyridine in 600 ml of toluene. After ½ h of stirring, the reaction medium is poured on water and the organic phase is washed with a solution of sodium bicarbonate, and then with a NaCl saturated solution. After concentration, the resulting product (84.5 g) is dissolved in 800 ml of ethanol to which are added 12.2 g (0.218 mol) of KOH as tablets. After ½ h of stirring, the reaction medium is poured on water and extracted with $CH_2Cl_2$. The organic phase is dried over $Na_2SO_4$ and concentrated. The aimed product is obtained after chromatography (silica, eluent: ethyl acetate 30, heptane 70) with a 63% yield.

$[\alpha]_D^{20} = -46.2°$ (c=1, $CH_3OH$);

IR (KBr) ν cm$^{-1}$: 1755, 1735;

$^1$H NMR (CDCl$_3$) δ ppm: 0 (6H); 1 (9H); 3.4 (3H); 3.6 (2H); 3.8–4.2 (2H); 4.7 (3H); 7.5 (4H);

m.p. <50° C.

Step 4: 3-[4-(hydroxymethyl)phenyl]-5(R)-methoxymethyl-2-oxazolidinone (code number MD 230248)

A solution of 29.2 g (0.083 mol) of compound MD 230247 and 7.8 g (0.025 mol) of tetrabutylammonium fluoride trihydrate in 200 ml of THF is stirred for 12 h at room temperature and the reaction medium is concentrated. The product is obtained after chromatography (silica, eluent: ethyl acetate 50, heptane 50);

m.p. = 65° C.;

IR (KBr) ν cm$^{-1}$: 3400, 1750, 1720, $^1$H NMR (CDCl$_3$) δ ppm: 2.4 exch. H; 3.35 (3H); 3.6 (2H); 3.8–4.2 (2H); 4.6 (2H); 7.35 (4H).

Step 5: 3-(4-carboxaldehydophenyl)-5(R)-methoxymethyl-2-oxazolidinone (code number MD 230256)

To a solution cooled at −60° C. of 12.46 g (0.0982 mol) of oxalyle chloride in 80 ml of methylene chloride, is added within 20 min. a solution of 12.76 g (0.1630 mol) of DMSO in 80 ml of methylene chloride. After 40 min., a solution of 19.6 g (0.0818 mol) of compound MD 230248 in 80 ml of methylene chloride is added, and then 1.4 g (0.409 mol) of triethylamine. After return to room temperature, 300 ml of water are added. The organic phase is washed with water, dried and concentrated. The product was obtained after purification by chromatography (silica, eluent: ethyl acetate 70, heptane 30) with a 80% yield;

m.p. = 96° C.;

$[\alpha]_D^{20} = -73.4°$ (c=1, $CH_2Cl_2$);

IR (KBr) ν cm$^{-1}$: 1740, 1690;

$^1$H NMR (CDCl$_3$) δ ppm: 3.4 (3H); 3.7 (2H); 3.8–4.3 (2H); 4.8 (1H); 7.8 (4H); 9.8 (1H).

Step 6: 3-[4-(4(R)-hydroxypentyl)phenyl]-5(R)-methoxymethyl-2-oxazolidinone (code number MD 230238).

A solution of 3.3 g (0.00712 mol) of 2(R)-hydroxypropyltriphenylphosphonium iodide (Helv. Chim. Acta, 59, 755-757, 1976), 1.34 g (0.00569 mol) of compound MD 230256 and 2.9 g (0.0213 mol) of $K_2CO_3$ in 10 ml of dioxane and 1.5 ml of formamide is heated under reflux for 20 h. After filtration and concentration, the resulting insaturated product is purified by dissolving it in 30 ml of DMF, and 0.58 g of imidazole and 0.94 g (0.00625 mol) of terbutyl dimethylchlorosilane are added. After 24 hours of stirring, the reaction medium is poured on water. The silylated product is extracted with methylene chloride and purified by chromatography (silica, eluent: ethyl acetate: 50 heptane: 50) with a 36% yield. 0.84 g of the resulting product is dissolved in 15 ml of THF in the presence of 0.65 g of tetrabutylammonium fluoride for 12 h. After concentration and purification by chromatography (silica, eluent: ethyl acetate: 70, heptane: 30), 0.53 g (0.0018 mol) of the purified insaturated product dissolved in 10 ml of methanol in the presence of (50% humidified) 10% palladium-carbon is hydrogenated under normal pressure. The aimed product is obtained with a 55% yield after chromatography (silica, ethyl acetate: 60, heptane: 40), $[\alpha]_D^{20}$: −45.8° (c=1, $CH_2Cl_2$)

IR (KBr) ν cm$^{-1}$: 3400, 1735;

m.p.: 47° C.;

$^1$H NMR (CDCl$_3$) δ ppm: 1.2 (3H); 1.5 (4H); 1.8 (1 exch. H); 2.6 (2H); 3.4 (3H); 3.6 (2H); 3.7–4.2 (3H); 4.7 (1H); 7.2 (2H); 7.4 (2H).

In the same manner, there was obtained:

3-[4-(4(S)-hydroxypentyl)phenyl]-5(R)-methoxymethyl-2-oxazolidinone (code number MD 230239);
m.p.: 53° C.; $[\alpha]_D^{20}$: −35.9° (c=1, $CH_2Cl_2$);
IR (KBr) $\nu$ cm$^{-1}$: 3400, 1740;
$^1$H NMR (CDCl$_3$) $\delta$ ppm: 1.1 (3H); 1.6 (5H of which 1 exch.); 3.4 (3H); 3.6 (2H); 3.7–4.2 (3H); 4.7 (1H); 7.1 (2H); 7.4 (2H).

It has to be noted that the above-mentioned insaturated product is the 3-[4-(4-hydroxy 1-pentylene)]-5(R)-methoxyethyl-2-oxazolidinone (code number MD 230319; $[\alpha]_D^{20}$: −38.8° (C=1, $CH_2Cl_2$); IR (microcell) $\nu$ cm$^{-1}$: 3500–3400, 1750; $^1$HNMR (CDCl$_3$) $\delta$ ppm: 1.2(3H);2.05(1H);2.4(2H); 3.4 (3H);3.6(2H);3.7–4.2(3H);4.7(1H);5.4–6.5(2H);7.4(4H).

Example 16

3-[4-[3-(2-methyl-1,3-dioxolane-2-yl)propyl]phenyl]-5(R)-methoxymethyl-2-oxazolidinone (code number MD 230084)

To a solution of 1.83 g (6.28 mmol) of compound MD 230083 (Ex. 13) in 25 ml of toluene, is added 0.382 g (6.28 mmol) of ethylene glycol and the mixture is heated under reflux for 12 h in the presence of p-toluene sulphonic acid while removing the water. The reaction mixture is concentrated. The residue is taken up in $CH_2Cl_2$. The organic phase is washed with NaHCO$_3$, and then with water, dried and concentrated. The product is purified by HPLC (silica, eluent: isopropyl ether: 65; heptane: 25: methanol: 10).
m.p.=81° C.:
$[\alpha]_D^{20}$= −49° (c=1 MeOH);
IR (KBr) $\nu$ cm$^{-1}$: 1740;
$^1$H NMR (CDCl$_3$) $\delta$ ppm: 1.25 (3H); 1.65 (4H) 2.55 (2H); 3.4 (3H); 3.6 (2H); 3.9 (6H); 4.65 (1H); 7.1 (2H); 7.4 (2H).

EXAMPLE 17

Step 1: 2,2-Dimethyl-4(S)-methoxymethyl-dioxolane (code number MD 370486)

To 910 ml of water, are added 910 g of NaOH as tablets, and then, at room temperature, 5 l of $CH_2Cl_2$, 44.4 g (0.195 mol) of benzyl triethylammonium chloride, 8,558.6 g (6.5 mol) of 2,2-dimethyl-3(S)-hydroxymethyldioxolane and 1,229.5 g (9.75 mol) of dimethyl sulphate. The reaction medium is stirred for 12 h and poured on water. The organic phase is concentrated. The product is distilled.
b.p.: 45° C. under 10 mm Hg
$[\alpha]_D^{20}$= +7.9° (c=4 CH$_3$OH);
IR (microcell) $\nu$ cm$^{-1}$=2995, 2940, 2820, 1380, 1370, 840;
$^1$H NMR (CDCl$_3$) $\delta$ ppm=1.2 (3H); 1.4 (3H); 3.35 (3H); 3.4–4.4 (3H); 4 (2H).

Step 2: 3-Methoxy-propane-1,2-diol(R) (code number MD 370487)

A solution of 950.3 g (6.5 mol) of compound MD 370486 in 4510 ml of water is heated at 60° C. and 3.2 ml of concentrated hydrochloric acid are added. Then 9 ml of triethylamine are added, and the reaction medium is concentrated and distilled with a 84% yield.
b.p.=66° C. under 1 mm Hg;
$[\alpha]_D^{20}$= −6.4° (c=4 CH$_3$OH);
IR (microcell) $\nu$ cm$^{-1}$: 3500, 3300, 2960, 2945, 2910;
$^1$H NMR (DMSOd$_6$) $\delta$ ppm: 3.2–3.7 (8H); 4.5 (2 exch. H)

Step 3: 3-methoxy-propane-1,2-diol(S)tosylate (code number MD 370488)

A solution of 371.4 g (3.5 mol) of compound MD 370487 in 100 ml of toluene is cooled at 13° C., and 565 ml of pyridine are added and then gradually a solution of 700.6 g (3.675 mol) of paratoluene sulphonic chloride in 775 ml of toluene is added. The reaction medium is then stirred for 12 h and poured on water. The organic phase is washed with 2N hydrochloric acid and concentrated. The product is obtained with a 58% yield after chromatography (silica, eluent: $CH_2Cl_2$: 50; petroleum ether: 50).
$[\alpha]_D^{20}$= +5.3° (c=4 CH$_3$OH);
IR (microcell) $\nu$ cm$^{-1}$: 3500, 1335, 1185, 1170;
$^1$H NMR (CDCl$_3$) $\delta$ ppm: 2.4 (3H); 3.1 (1 exch H) 3.2–3.6 (5H); 3.8–4.2 (3H).

Step 4: 3-[4-[3-(2-methyl-1,3-dioxolane-2-yl)propyl]phenyl]-5(R)-methoxymethyl-2-oxazolidinone (code number MD 230084)

To 8.9 g (0.0887 mol) of phosgene in 120 ml of dichloroethane, are added 5.4 g (0.059 mol) of compound MD 370488, and then 13.3 g (0,0887 mol) of dimethylaniline dissolved in 20 ml of dichloroethane. The reaction medium is stirred for 1 h 30 at 50° C. After cooling, the latter is washed with iced water and dried over sodium sulphate. This solution is added to a solution of 13 g (0.059 mol) of compound MD 230113 (Ex. 12—Step 3) and 7.2 g (0.059 mol) of 4-dimethylaminopyridine in 200 ml of dichloroethane. The reaction medium is then heated under reflux for 30 min., cooled and poured on water. The organic phase is washed with a solution of sodium bicarbonate, dried and concentrated. The product is obtained after chromatography (silica, eluent: isopropyl ether: 65; heptane: 25; CH$_3$OH: 10) with a 47% yield and has the same physical characteristics as those of the compound obtained in Example 16.

EXAMPLE 18

3-[3-bromo-4-(4,4,4-trifluoro-3(R)-hydroxybutoxy)-phenyl]-5(R)-methoxymethyl-2-oxazolidinone (code number MD 230237)

To the solution of 2 g (0.00572 mol) of compound MD 370503 (Ex. 7) in 8 ml of acetic acid, is added 1.83 g (0.01145 mol) of bromine dissolved in 10 ml of acetic acid. The reaction medium is stirred for 2 h and poured on iced water. The aqueous phase is extracted with methylene chloride and ethyl acetate. The organic phase is dried over Na$_2$SO$_4$ and concentrated. The product is purified by chromatography (silica, eluent: $CH_2Cl_2$: 98; MeOH: 2);
m.p.: 87° C.; $[\alpha]_D^{20}$: −14.8° (c=1, $CH_2Cl_2$);
IR (KBr) $\nu$ cm$^{-1}$: 3360, 3400, 1760, 1725;
$^1$H NMR (CDCl$_3$) $\delta$ ppm: 2.1 (2H); 3.4 (3H); 3.6 (2H); 3.7–4.9 (7H); 6.8 (1H); 7.5 (1H); 7.6 (1H).

EXAMPLE 19

3-[4-[2-(1-hydroxy-1-cyclohexylethoxy]phenyl]-5(R) methoxymethyl-2-oxazolidinone (code number MD 360331).

Step 1: 1-(2-mesyloxyethyl)-1-cyclohexanol (MD 360342)

This compound is obtained from 1-(2-hydroxyethyl)-cyclohexanol (Org. Prep. Proc. 16, 321, 1984) according to the procedure of Step 5 of Example 7, wherein mesyl chloride is used instead of tosyl chloride. Liquid;
Elemental analysis:
Calc. % C: 48 62; H: 8.16
Found % C: 47.71; H: 8.43

Step 2: 3-[4-[2-(1-hydroxy-1-cyclohexyl)ethoxy]-phenyl]-5(R)-methoxymethyl-2-oxazolidinone (code number 360331)

This compound is obtained according to the procedure of Step 6 of Example 7, using compounds MD 360342 and MD 200405. Yield =75%;

m.p.: 87° C.; $[\alpha]_D^{20}$: −47.6° (c=1, $CH_3OH$).

EXAMPLE 20

3-[4-(3-methyl-3-hydroxybutoxy)phenyl]-5(R)-methoxymethyl-2-oxazolidinone (code number MD 360335)

Step 1: 3-methyl-1-mesyloxy-3-butanol (MD 360359)

This compound is obtained according to the procedure of Step 5 of Example 7, using mesyl chloride instead of tosyl chloride. Liquid;

IR (microcell) $v$ cm$^{-1}$: 3520-3400, 1350-1170, 950;

$^1$H NMR ($CDCl_3$) $\delta$ppm: 1.3 (6H); 2 (2H); 2.6 (1 exch. H); 3 (3H); 4.4 (2H).

Step 2: 3-[4-(3-methyl-3-hydroxybutoxy)phenyl]-5(R)-methoxymethyl-2-oxazolidinone (MD 360335)

This compound is obtained according to Step 6 of Example 7, using compounds MD 360539 and MD 200405.

m.p.: 52° C.; $[\alpha]_D^{20}$: −40.4° (c=1, $CH_2Cl_2$);

IR (KBr) $v$ cm$^{-1}$: 3480, 1745

$^1$H NMR ($CDCl_3$) $\delta$ ppm: 1.4 (6H); 2 (2H); 2.6 (1 exch. H) 3.4 (3H); 3.6 (2H); 3.8-4.4 (4H); 4.7 (1H); 6.9 (2H); 7.4 (2H).

In the same manner, from compound MD 200405 and 5,5,5,4,4-pentafluoro-3-hydroxypentanol tosylate (MD 360410), there was obtained:

3-[4-(5,5,5,4,4-pentafluoro-3-hydroxypentoxy)phenyl]-5(R)-methoxymethyl-2-oxazolidinone (MD 360328)

$^1$H NMR ($CDCl_3$) $\delta$ ppm: 2.15 (2H); 3 (1 exch. H); 3.4 (3H); 3.6 (2H); 3.7-4.3 (5H); 4.6 (1H); 6.85 (2H).

Compound MD 360410 was obtained according to the procedure of Step 5 of Example 7, from pentafluoropentane-1,3-diol (J. Fluorine Chem. 42, 17, 1989). The data of $^1$H NMR of compound MD 360410 are as follows: ($CDCl_3$) $\delta$ ppm: 1.7-2.5 (2H); 2.45 (3H); 2.8 (1 exch. H); 3.85-4.6 (3H); 7.35 (2H); 7.8 (2H).

EXAMPLE 21

3-[4-(4,4,4-trifluoro-3-hydroxybutoxy)phenyl]-5(R)-methoxymethyl-2-oxazolidinone (code number MD 230016)

Step 1: 4-nitro-1-[4,4,4-trifluoro-3-(1-ethoxyethoxy)-butoxy]benzene (MD 360349)

To a suspension of 2.4 g (0.049 mol) of 50% NaH in 50 ml of THF, is slowly added a solution of 10.6 g (0.049 mol) of 3-(1-ethoxyethoxy)-4,4,4-trifluoro-1-butanol in 15 ml of THF. When no more gas evolves, a solution of 6.5 g (0.041 mol) of 4-chloronitrobenzene in 65 ml of DMF is added. After 30 min., the reaction medium is poured on iced water. The reaction medium is extracted with ether. The organic phase is washed with water, dried over $Na_2SO_4$ and concentrated. The aimed product is obtained with a 78% yield after recrystallization from isopropanol. m.p.: 81° C.;

IR (KBr) $v$ cm$^{-1}$: 1610-1590; 1510-1500; 1340-1250; 1165-1110;

$^1$H NMR ($CDCl_3$) $\delta$ ppm: 1.15 (3H); 1.25 (3H); 2.2 (3H); 3.6 (2H); 4.2 (3H); 4.8 (1H); 6.95 (2H); 8.2 (2H).

In the same manner, there were obtained the following compounds:

4-nitro-1-(4,4,4-trifluoro-3(R)-hydroxybutoxy)benzene (MD 360363) from 4,4,4-trifluoro-3(R)-hydroxy-1-butanol:

m.p.: 80° C.: Yield: 10%:

IR (KBr) $v$ cm$^{-1}$: 3500, 1300-1360;

$^1$H NMR ($CDCl_3$) $\delta$ ppm: 1.9-2.5 (2H); 3.7 (1H); 4-4.6 (3H); 6.9 (2H); 8 (2H);

4-nitro-1-(3-hydroxybutoxy)benzene (MD 360364) from 3-hydroxy-1-butanol:

$^1$H NMR ($CDCl_3$) $\delta$ ppm: 1.25 (3H); 1.65 (1 exch. H) 2 (2H); 3.8 (1H); 6.9 (2H); 8.2 (2H);

4-nitro-1-(4-hydroxypentoxy)benzene (MD 360377) from 4-hydroxy-1-pentanol:

IR (microcell) $v$ cm$^{-1}$: 3400, 1610-1590, 1500;

$^1$H NMR ($CDCl_3$) $\delta$ ppm: 1.25 (3H); 1.4-2.2 (8H); 3.75 (1H); 4.05 (2H); 6.9 (2H); 8.15 (2H).

Step 2: 4-[4,4,4-trifluoro-3-(1-ethoxyethoxy)butoxy]aniline (MD 370350)

This compound was obtained by hydrogenating compound MD 360349 with a 52% yield (the same procedure as Step 2 of Example 15).

IR (microcell) $v$ cm$^{-1}$: 3440, 3360, 1510-1670, 1300-1000;

$^1$H NMR ($CDCl_3$) $\delta$ ppm: 0.8-1.4 (6H); 2.05 (2H); 3-3.8 (5H); 3.8-4.4 (3H); 6.45-6.85 (4H).

In the same manner, there was obtained from compound MD 360364:

4-(3-hydroxybutoxy)aniline (MD 360365)

m.p.: 90° C.;

IR (KBr) $v$ cm$^{-1}$: 3350-3240, 3200, 1510, 1240;

$^1$H NMR ($CDCl_3$) $\delta$ ppm: 1.25 (3H); 1.85 (2H) 3.1 (3 exch. H); 4 (3H); 6.45-6.9 (4H).

Step 3: 4-[4,4,4-trifluoro-3-(1-ethoxyethoxy)butoxy]-N-ethoxycarbonylaniline (MD 360351)

This compound was obtained according to the procedure of Step 2 of Example 23. Yield: 85%; oil;

IR (microcell) $v$ cm$^{-1}$: 3320, 1710-1730;

$^1$H NMR ($CDCl_3$) $\delta$ppm: 0.8-1.4 (9H); 2.05 (2H); 3.45 (2H); 3.8-4.45 (5H); 4.8 (1H); 6.5 (1 exch. H); 6.8 (2H); 7.25 (2H).

In the same manner, there was obtained from compound MD 360365:

4-(3-hydroxybutoxy)-N-ethoxycarbonylaniline (MD 360366)

m.p.: 86° C.;

IR (KBr) $v$ cm$^{-1}$: 3430-3300, 1705;

$^1$H NMR ($CDCl_3$) $\delta$ ppm: 1.2 (6H); 1.85 (2H); 2.3 (1 exch. H); 3.8-4.4 (4H); 6.8 (3H of which 1 exch.); 7.25 (2H).

Step 4: 3-[4-(4,4,4-trifluoro-3-(1-ethoxyethoxy)butoxy)phenyl]-5(R)-methoxymethyl-2-oxazolidinone (MD 360352)

This compound was obtained according to the procedure of Step 3 of Example 23. Oil;

$^1$H NMR ($CDCl_3$) $\delta$ ppm: 0.8-1.4 (6H); 2.1 (2H); 3.4 (3H); 3.6 (2H); 3.8-4.4 (5H); 4.6-5 (2H); 6.8 (2H); 7.4 (2H).

In the same manner, from compound MD 360366, there was obtained MD 370284 having the same physical characteristics as those indicated in Example 6.

Step 5: 3-[4-(4,4,4-trifluoro-3-hydroxybutoxy)-phenyl]-5(R)-methoxymethyl-2-oxazolidinone (code number MD 230016)

This compound was obtained by treating compound MD 360352 according to the procedure of Step 4 of Example 4. The product is obtained with a 40% yield. This compound has the same physical characteristics as those given in Example 7.

EXAMPLE 22

3-[4-(5,5,5-trifluoro-4-hydroxypentyl)phenyl]-5(R)-methoxymethyl-2-oxazolidinone (code number MD 360207)

Step 1: 4,4,4-trifluoro-1-iodo-3-butanol (MD 360253)

To a solution of 2.04 g (o.0068 mol) of compound MD 370272 (4,4,4-trifluoro-1-tosyloxy-3-butanol) in 20 ml of acetone, are added 2.56 g (0.0171 mol) of KI and the mixture is heated under reflux overnight. After filtration and concentration, the product is obtained after chromatography (silica, eluent: heptane 80, ethyl acetate 20).

IR (microcell) $\nu$ cm$^{-1}$: 3400;

$^1$H NMR (CDCl$_3$) $\delta$ ppm: 1.9–2.5 (2H); 2.4 (1 exch. H); 3.35 (2H); 4.2 (1H).

Step 2: 4,4,4-trifluoro-3-hydroxybutyltriphenylphosphonium iodide (MD 360254)

35.6 g (0.14 mol) of compound MD 360253 and 36.8 g (0.14 mol) of triphenylphosphine in dioxane are heated under reflux overnight. The product is filtered and dried. Yield: 72%; m.p.: 159° C.

Step 3: 2,2,2-trifluoro-1-para-nitrocinnamylethanol (MD 360255)

A solution of 13 g (0.086 mol) of paranitrobenzaldehyde, 55.57 g (0.108 mol) of compound MD 360254 and 44.78 g (0.324 mol) of K$_2$CO$_3$ is heated under reflux for 4 hours. The reaction medium is poured on water and extracted with ethyl acetate. The organic phase is dried over Na$_2$SO$_4$ and concentrated. The product is obtained after chromatography (silica, eluent: CH$_2$Cl$_2$) Yield: 73%; m.p.: 71° C.;

IR (KBr) $\nu$ cm$^{-1}$: 3480, 1595–1510, 1340;

$^1$H NMR (CDCl$_3$) $\delta$ ppm: 2.6 (2H); 2.85 (1 exch. H); 4.15 (1H); 6.5 (2H); 7.4 (2H); 8.1 (2H).

Step 4: 1,1,1-trifluoro-5-(4-aminophenyl)-2-pentanol (MD 360256)

This compound was obtained by hydrogenating compound MD 360255 according to the procedure of Step 2 of Example 12. Yield: 78%; m.p.: 90° C.;

IR (KBr) $\nu$ cm$^{-1}$: 3420–3330, 3150, 1620, 1515, 1280, 1260, 1180, 1120;

$^1$H NMR (CDCl$_3$) $\delta$ ppm: 1.6 (4H); 2.5 (2H) 3.6 (3H) 4.6 (1 exch H; 6.6 (2H); 6.9 (2H).

Step 5: 3-[4-(5,5,5-trifluoro-4-hydroxypentyl)phenyl]-5(R)-methoxymethyl-2-oxazolidinone (code number MD 360207)

This compound was obtained according to the procedure of Step 4 of Example 17: oil;

IR (microcell) $\nu$ cm$^{-1}$; 3410, 1735;

$^1$H NMR (CDCl$_3$) $\delta$ ppm: 1 (4H); 2.7 (2H); 3.4 (3H); 3.6 (3H of which 1 exch.); 4 (1H); 4.7 (1H); 7.1 (2H); 7.4 (2H).

EXAMPLE 23

3-(4-benzyloxyphenyl)-5(R)-methoxymethyl-2-oxazolidinone (MD 200404)

Step 1: 4-Methoxymethyl-1,3-dioxolane-2-one (S) (code number MD 360287)

A mixture of 14 g (0.132 mol) of 3-methoxypropane-1,2-diol (S) and 31.16 g (0.264 mol) of diethyl carbonate in the presence of 0.108 g of 50% sodium hydride is heated until distillation of the alcohol formed. After completion of the reaction, the aimed product is distilled.

b.p.$_{0.3}$: 117° C.; Yield: 93%;

$[\alpha]_D^{20}$: −32.2° (c=1, CH$_2$Cl$_2$);

IR (microcell) $\nu_{CO}$: 1790 cm$^{-1}$;

$^1$H NMR (CDCl$_3$) $\delta$ ppm: 3.4 (3H); 3.6 (2H); 4.3–4.9 (3H)

Step 2: N-ethoxycarbonyl 4-benzyloxy-aniline (MD 360343)

To a solution of 10 g (10$^{-3}$ mol) of 4-benzyloxyaniline in 90 ml of THF and 10 ml of water, are added 6.3 g of sodium bicarbonate, and then 5.28 ml (55×10$^{-3}$ mol) of ethyl chloroformate. After 18 h of stirring, the reaction medium is filtered and concentrated. The residue is taken up in ethyl acetate. The organic solution is washed with water, dried over Na$_2$SO$_4$ and concentrated. The product is obtained with a 91% yield.

m.p.=98° C.;

IR (KBr) $\nu$ cm$^{-1}$: 3320, 1700, 1510–1530, 1230;

$^1$H NMR (CDCl$_3$) $\delta$ ppm: 1.2 (3H); 4.2 (2H); 5 (2H); 6.7 (1H); 6.9 (2H); 7.2 (2H).

Step 3: 3-(4-benzyloxyphenyl)-5(R)-methoxymethyl-2-oxazolidinone (MD 200404)

1 g (3.6×10$^{-3}$ mol) of compound MD 360343, 0.099 g (0.72×10$^{-3}$ mol) of K$_2$CO$_3$ and 0.586 g (4.5×10$^{-3}$ mol) of compound 360287 (obtained in Step 1) are heated at 160° C. under stirring for 3 h. After cooling, the reaction medium is taken up in methylene chloride, washed with water, dried over Na$_2$SO$_4$, and concentrated. The product is recrystallized from isopropanol. Yield =71%. It has the same physical characteristics as those of compound of the Example 2.

EXAMPLE 24

3-[4-[3-(2-phenylmethyl-1,3-dioxolane-2-yl)propyl]-phenyl]-5(R)-methoxymethyl-2-oxazolidinone (code number MD 360334)

Step 1: 2-[2-(phenylmethyl)-1,3-dioxolane-2-yl]ethanol (code number 360370)

This compound is obtained according to the method described in Step 2 of Example 4, from [2-(phenylmethyl)-1,3-dioxolane-2-yl]acetic acid ethyl ester (Synthesis 451, 1982):

IR (microcell) $\nu$ cm$^{-1}$: 3440–3400

$^1$H NMR (CDCl$_3$) $\delta$ ppm: 1.9 (2H); 2.8 (3H of which 1 exch.); 3.5–4 (6H); 7.2 (5H);

Step 2: 2-(phenylmethyl)-2-(2-bromoethyl)-1,3-dioxolane (code number 360371)

To a solution of 37.8 g (0.181 mol) of compound 360370 in 200 ml of CH$_2$Cl$_2$, are added 120.4 g (0.363 mol) of CBr$_4$, and then gradually 95.2 g (0.363 mol) of triphenylphosphine, and then the reaction medium is stirred at room temperature for ½ hour. After filtration, the organic phase is concentrated. Yield: 81%;

IR (microcell) $\nu$ cm$^{-1}$: 3020, 2960, 2880, 1605;

$^1$H NMR (CDCl$_3$) $\delta$ ppm: 2.2 (2H); 2.8 (2H); 3.4 (2H) 3.8 (4H); 7.2 (5H).

Step 3: [[2-(phenylmethyl)-1,3-dioxolane-2-yl]ethyl]-triphenylphosphonium bromide (code number 360372)

To a solution of 33 g (0.1217 mol) of compound 360371 in 200 ml of dioxane, are added 31 g (0.1217 mol) of triphenylphosphine and the mixture is heated for 20 hours. After cooling, the precipitate is filtered and washed with dioxane and ethyl ether. Yield: 81%;

m.p.=225° C.;

$^1$H NMR (CDCl$_3$) $\delta$ ppm: 1.6–2.2 (2H); 3 (2H); 3.2–4.2 (6H); 7.2 (5H); 7.5–7.9 (15H).

In the same manner, there were obtained [2-(2-phenyl-1,3-dioxolane-2-yl)ethyl]triphenylphosphonium bromide m.p.: 228° C.;

$^1$H NMR (CDCl$_3$) δ ppm: 2–2.5 (2H); 3.4–4.4 (6H); 7.4 (5H); 7.6–8 (15H) from 2-phenyl-2-(2-bromoethyl)-1,3-dioxolane (Tetrahedron Letters, 1987, 28, 1397).

[2-(2-cyclohexyl-1,3-dioxolane-2-yl)ethyl]triphenylphosphonium bromide from 2-cyclohexyl-2-(2-bromoethyl)-1,3-dioxolane (ex. 27): Liq., IR (microcell) ν cm$^{-1}$: 2920–2850, 1440–1110;
$^1$H NMR (CDCl$_3$) δ ppm: 0.9–2.3 (13H); 3–4.2 (6H); 7.6–8 (15H).

Step 4: 2-(Para-nitrocinnamyl)-2-(phenylmethyl)-1,3-dioxolane (code number 360373)

This compound is obtained according to the procedure of Step 3 of Example 22: liquid;

IR (microcell) ν cm$^{-1}$: 1595, 1510, 1340;
$^1$H NMR (CDCl$_3$) δ ppm: 2.6 (2H); 3 (2H); 3.9 (4H); 5.8–6.8 (2H); 7.3 (5H); 7.4 (2H); 8.2 (2H).

In the same manner, there were obtained:
2-(para-nitrocinnamyl)-2-phenyl-1,3-dioxolane (code number 360384)

IR (microcell) ν cm$^{-1}$: 1595, 1510, 1340,
$^1$H NMR (CDCl$_3$) δ ppm: 2.8–3 (2H); 3.6–4.2 (4H) 5.6–6.8(2H); 7.15–7.65 (7H); 8.1 (2H);
m.p.=82° C.;

2-(para-nitrocinnamyl)-2-cyclohexyl-1,3-dioxolane (code number 360416)

IR (microcell) ν cm$^{-1}$: 2920–2850, 1595–1510, 1390,
$^1$H NMR (CDCl$_3$) δ ppm: 0.8–2.1 (11H); 2.5–2.8 (2H); 4 (4H); 5.7–6.7 (2H); 7.45 (2H); 8.2 (2H).

Step 5: 2-[3-(4-aminophenyl)propyl]-2-(phenylmethyl)-1,3-dioxolane (code number 360374)

This compound is obtained according to the procedure of Example 22 (step 4):
m.p.=55° C.;
IR (KBr) ν cm$^{-1}$: 3450–3360, 1620–1510;
$^1$H NMR (CDCl$_3$) δ ppm: 1.65 (4H); 2.45 (2H); 2.85 (2H); 3.45 (2 exch. H); 3.45–4 (4H); 6.5 (2H); 6.9 (2H); 7.2 (5H).

In the same manner, there were obtained:
2-[3-(4-aminophenyl)propyl]-2-phenyl-1,3-dioxolane (code number 360385)
m.p.=68° C.;
IR=(KBr) ν cm$^{-1}$: 3440–3360, 1630–1610, 1515;
$^1$H NMR (CDCl$_3$) δ ppm: 1.4–2.2 (4H); 2.4 (2H); 3.45 (2H); 3.6–4.15 (4H); 6.5 (2H); 6.9 (2H); 7.2–7.6 (5H);

2-[3-(4-aminophenyl)propyl]-2-cyclohexyl-1,3-dioxolane (code number 360417)
IR (microcell) ν cm$^{-1}$: 3440–3360, 1625;
$^1$H NMR (CDCl$_3$) δ ppm: 0.8–2 (11H); 2.4 (2H); 3.45 (2 exch. H); 3.8 (4H); 6.5 (2H); 6.9 (2H).

Step 6: 2-[3-[4-(ethoxycarbonylamino)phenyl]propyl]-2-(phenylmethyl)-1,3-dioxolane (code number 360375)

This compound is obtained according to the procedure of Step 2 of Example 23.

$^1$H NMR (CDCl$_3$) δ ppm: 1.25 (3H); 1.65 (4H); 2.5 (2H); 2.85 (2H); 3.7 (4H); 4.2 (2H); 6.9 (1 exch. H); 7–7.4 (9H).

In the same manner, there were obtained:
2-[3-[4-(ethoxycarbonylamino)phenyl]propyl]-2-phenyl-1,3-dioxolane (code number 360386)
$^1$H NMR (CDCl$_3$) δ ppm: 1.25 (3H); 1.4–2.2 (4H); 2.5 (2H); 3.5–4 (4H); 4.2 (2H); 6.6–7.6 (10H of which 1 exch.);
m.p.=66° C.

2-[3-[4-(ethoxycarbonylamino)phenyl]propyl]-2-cyclohexyl-1,3-dioxolane (code number 360420)
m.p.=70° C.
IR (KBr) ν cm$^{-1}$: 3360, 1705.

Step 7: 3-[4-[3-(2-phenylmethyl-1,3-dioxolane-2-yl)propyl]phenyl]-5(R)-methoxymethyl-2-oxazolidinone (code number 360334)

This compound is obtained according to the procedure of Step 3 of Example 23.

$^1$H NMR (CDCl$_3$) δ ppm: 1.6 (4H); 2.5 (2H); 2.85 (2H); 3.4 (3H); 3.45–4.2 (8H); 4.65 (1H); 6.9–7.6 (9H).
[α]$_D^{20}$:−33.2° (c=1, CH$_2$Cl$_2$);

In the same manner, there were obtained:
3-[4-[3-(2-phenyl-1,3-dioxolane-2-yl)propyl]phenyl]-5(R)-methoxymethyl-2-oxazolidinone (code number 360332)
$^1$H NMR (CDCl$_3$) δ ppm: 1.4–2.1 (4H); 2.55 (2H); 3.4 (3H); 3.6 (2H); 3.6–4.2(6H); 4.65 (1H); 6.95–7.95(9H);
IR (KBr) ν cm$^{-1}$: 1750;
[α]$_D^{20}$=−31.9° (c=1, CH$_2$Cl$_3$)

3-[4-[3-(2-cyclohexyl-1,3-dioxolane-2-yl)propyl]phenyl]-5(R)-methoxymethyl-2-oxazolidinone (MD 360354)
m.p.=86° C.; IR (KBr) ν cm$^{-1}$: 1740–1730.

EXAMPLE 25

3-[4-(5-phenyl-4-oxopentyl)phenyl]-5(R)-methoxymethyl-2-oxazolidinone (MD 360394)

This compound was obtained from compound MD 360334 (Example 24) subjected to the procedure of Example 9. Yield: 58%.; m.p. 105° C.;
[α]$_D^{20}$: −35.9° (c=1, CH$_2$Cl$_2$);
$^1$H NMR (CDCl$_3$) δ ppm: 1.9 (2H); 2.5 (4H); 3.4 (3H); 3.6 (2H); 3.65 (2H); 3.95 (2H); 4.7 (1H); 7.1 (2H); 7.25 (5H); 7.45 (2H);
IR (KBr) ν cm$^{-1}$: 1740, 1710.

In the same manner, there were obtained, from the corresponding dioxolanes:
3-[4-(4-phenyl-4-oxobutyl)phenyl]-5(R)-methoxymethyl-2-oxazolidinone (MD 360401);
IR (microcell) ν cm$^{-1}$: 3450, 1750;
$^1$H NMR (CDCl$_3$) δ ppm: 1.6–1.8 (4H of which 2 exch.); 2.6 (2H); 3.4 (3H); 3.6 (2H); 3.7–4.2 (2H); 4.4–4.8 (2H); 7–7.4 (9H);

3-[4-(4-cyclohexyl-4-oxobutyl)phenyl]-5(R)-methoxymethyl 2-oxazolidinone (MD 360399)
m.p.=86° C.; [α]$_D^{20}$: −35.4° (C=1, CH$_2$Cl$_2$)
$^1$H NMR (CDCl$_3$) δ ppm: 0.9–2.2 (13H); 2.2–2.7 (4H); 3.4 (3H); 3.6 (2H); 3.7–4.2 (2H); 4.6 (1H); 7.1 (2H); 7.4 (2H).

EXAMPLE 26:

3-[4-(5-phenyl-4-hydroxypentyl)phenyl]-5(R)-methoxymethyl-2-oxazolidinone (MD 360395)

This compound was obtained from compound MD 360394 subjected to the procedure of Example 14.

$^1$H NMR (CDCl$_3$) δ ppm: 1.6–1.9 (5H of which 1 exch.); 2.7 (4H); 3.4 (3H); 3.6 (2H); 3.7–4.2 (3H) ; 4.7 (1H); 7–7.5 (9H);
m.p.=72° C.

In the same manner, there were obtained from the corresponding ketones:
3-[4-(4-phenyl-4-hydroxybutyl)phenyl]-5(R)-methoxymethyl-2-oxazolidinone (MD 360402)
IR (microcell) ν cm$^{-1}$: 3450, 1750;
$^1$H NMR (CDCl$_3$) δ ppm: 1.6–1.8 (4H); 2.6 (2H); 3.4 (3H); 3.6 (2H); 3.7–4.2 (2H); 4.4–4.8 (2H); 7–7.4 (9H).
3-[4-(4-cyclohexyl-4-hydroxybutyl)phenyl]-5(R)-methoxymethyl-2-oxazolidinone

EXAMPLE 27

2-cyclohexyl-2-(2-bromoethyl)-1,3-dioxolane (code number 360414)

Step 1: 3-bromo-1-cyclohexyl-propanone

In a solution of 1-cyclohexyl-1-one-2-propene (0.255 mol) in 200 ml of $CH_2Cl_2$, cooled at 10°–15° C., HBr gas is bubbled through. After completion of the reaction, the reaction medium is washed with an aqueous $NaHCO_3$ saturated solution, dried over $Na_2SO_4$ and concentrated to obtain the aimed product as an oil.

Step 2: 2-cyclohexyl-2 (2-bromoethyl)-1,3 dioxolane

A solution of the compound obtained in the previous step (0.223 mol) in 600 ml of benzene, this solution further comprising 0.58 mol of ethylene glycol and 2.5 g of paratoluene sulphonic acid is refluxed while removing the formed water. After 3 hours 30 min. of reaction the solution is poured ;n a saturated NaCl solution the organic phase is dried over $Na_2SO_4$, concentrated and purified by chromatography (silica, eluent heptane 60-$CH_2Cl_2$40).

EXAMPLE 28

3-[4-(4,4,4-trifluoro-3(R)-methoxy butoxy)phenyl]-5(R)-methoxymethyl-2 oxazolidinone (code number MD 360316)

To a solution of $2.29 \times 10^{-2}$ mol of compound MD 370503 (Ex. 7 in 80 ml of toluene, is added $2.29 \times 10^{-3}$ mol of tertiobutylammonium bromide, $6.8 \times 10^{-2}$ mol of methyl sulphate and 7.3 ml of 50 % aqueous NaOH. The reaction medium is stirred for 1 hr. and poured on ethyl acetate. The organic phase is washed with water, dried on $Na_2SO_4$ and concentrated. The aimed product is obtained with a yield of 86 % after chromatography (silica, eluent: ethyl acetate 40-heptane 60).

$[\alpha]_D^{20}$: +1.2° (C=1 $CH_2Cl_2$); IR (microcell) $\nu$ cm$^{-1}$: 1750:

$^1$HNMR (CDCl$_3$) $\delta$ ppm: 1.8–2.3 (2H); 3.4 (3H); 3.5 (3H) ; 3.6 (2H); 3.8–4.3 (5H); 4.7 (1H); 6.9 (2H); 7.45 (2H).

The following compound is obtained by the same procedure:

3-[4-(4,4,4 -trifluoro-3(R)-benzyloxy butoxy)phenyl]-5(R)-methoxymethyl-2-oxazolidinone (code number MD 360317):

$[\alpha]_D^{20}$: +49° (C=1, $CH_2Cl_2$); IR (microcell) $\nu$ cm$^{-1}$: 1750;

$^1$HNMR (CDCl$_3$) $\delta$ ppm: 1.8–2.2 (2H); 3.3 (3H); 3 6 (2H); 3.7–4.1 (5H); 4.3–4.9 (3H) 6.7 (2H); 7.1 (5H); 7.3 (2H).

EXAMPLE 29

Racemate mixture of 3-[4-(4,4,4-trifluoro-3-hydroxybutoxy)phenyl]-5-methoxymethyl-2-oxazolidinone (code number 370167):

Obtained by the procedure of example 5.

m.p.=89° C.; $^1$HNMR (CDCl$_3$) $\delta$ ppm: 2.05 (2H); 3.4 (3H); 3.5 (1H); 3.6 (2H); 4 (5H); 4.7 (1H); 6.8 (2H); 7.3 (2H).

The derivatives of formula (I) have been studied on experimental animals and showed pharmacological activities especially in the psychotropic field, particularly as potential antidepressants and anxiolytics.

The antidepressive activity has been demonstrated by the 5-HTP potentialisation assay in rat according to the procedure described by: M. JALFRE, B. BUCHER, A. COSTON, G. MOCQUET and R. D. PORSOLT: Arch. Int. Pharmacodyn. (1982), 259, 194–221. The dose of product which, when given orally, brings about in 50% of the animals (ED$_{50}$) the appearance of generalized shakings or of stereotypies (trinklings, shakes of head) consecutive to the administration by intraperitoneal route 1 h after the first treatment of 5-hydroxy-tryptophane (5-HTP) is determined in rat. The results obtained with some compounds according to the invention in the previously mentioned assay are set forth, by way of example, in the table below, in which is also mentioned the acute toxicity (LD$_{50}$) of some of the tested compounds and which is evaluated in mouse acording to the method of J. T. LITCHFIELD and F. WILCOXON (J. Pharmacol. Exp. Ther. (1949), 96, 99).

TABLE

| TESTED COMPOUND CODE NUMBER | ED$_{50}$ mg/kg | LD$_{50}$ mg/kg p.o. |
|---|---|---|
| MD230197 | 2.4 | |
| MD230201 | 1.6 | |
| MD230238 | 1.9 | |
| MD370503 | 0.14 | 2500 |
| MD370120 | 0.83 | 1400 |
| MD370122 | 0.68 | |
| MD370504 | 1.8 | |
| MD370047 | 1.9 | |
| MD370167 | 1.1 | |
| MD230082 | 1.1 | |
| TOLOXATONE | 30 | |

The previoulsy mentioned results show that the compounds which make the subject-matter of the present invention can be used for the preparation of psychotropic drugs and particularly potential antidepressants and anxiolytics, these drugs finding their use in therapy particularly for the treatment of endogenous and exogenous depressive states.

These drugs can be administred to humans or any warm-blooded animals in a variety of pharmaceutical forms well-known in the art and particularly in the form of compositions formulated for their administration by an oral, injectable or rectal route.

For the orally administration, said compositions can take the form of tablets, dragees or capsules prepared by the conventional techniques using known carriers and excipients, such as binding agents, fillers, lubricants and desintegration agents; they can also be in the form of solutions, syrups or suspensions.

For the administration in the form of an injectable solute, the compositions according to the invention may be in the form of injectable solutions, suspensions or emulsions containing an acceptable oily or aqueous liquid carrier.

For the rectal administration, the compositions may be in the form of suppositories containing the conventional bases for suppositories.

The therapeutic active dose of the active principles, i.e. of the derivatives (I) and of the pharmaceutically acceptable salts thereof, depends particularly on the administration route, the patient's body weight and on the therapeutic potency of the used active principles.

By oral route, the given doses may generally reach 10 mg/kg/day of active principle (in one or more intakes); by injectable route, they may reach 1 mg/kg/day (in one or more intakes); by rectal route, they may reach 5 mg/kg/day of active compound (in one or more suppositories).

We claim:

1. The derivatives of the formula:

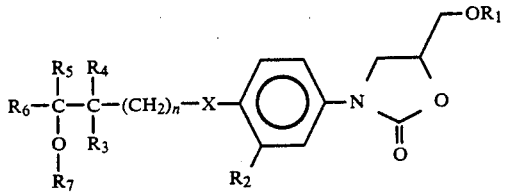

(I)

wherein:
$R_1$ is H or $C_1$-$C_4$ alkyl;
X is either an oxygen atom, in which case $R_2$=H or halogen, or a methylene group or a —CH=CH— group, in which case $R_2$=H;
n is 1 or 2 when X is an oxygen atom or a methylene group and 0 or 1 when X is a —CH=CH— group;
each of $R_3$ and $R_4$ is independently H, $C_1$-$C_4$ alkyl $C_4$-$C_7$ cycloalkyl, phenyl or benzyl;
$R_5$ is H or $C_1$-$C_4$ alkyl;
$R_6$ is $C_1$-$C_4$ alkyl, $CHF_2$, $CF_3$, $CF_3CF_2$, $C_1$-$C_4$ cycloalkyl, phenyl or benzyl;
$R_4$ and $R_6$ may further form together a —$(CH_2)_3$— or —$(CH_2)_4$— chain;
$R_5$ and $R_6$ may further form together a —$(CH_2)_4$— or —$(CH_2)_5$— chain; and
$R_7$ is H, $C_1$-$C_4$ alkyl, $C_2$-$C_5$ acyl or benzyl, these derivatives being under the form of diastereoisomers or enantiomers or under the cis- or trans-form or under the form of a mixture of all theses forms, including the racemic forms.

2. The derivatives according to claim 1, wherein:
$R_1$=H or $CH_3$;
$R_2$=H;
X=oxygen or $CH_2$;
n=1 or 2;
$R_3$, $R_4$ and $R_5$ are H or $CH_3$;
$R_6$ is $CH_3$ or $CF_3$; and
$R_7$ is H, $CH_3$ or acetyl.

3. The derivatives according to claim 1, wherein:
$R_1$=$CH_3$;
$R_2$=H;
X=oxygen;
n=1 or 2;
$R_3$=$R_4$=$R_5$=H;
$R_6$=$CF_3$; and
$R_7$=H.

4. The derivatives according to claim 1, wherein:
$R_1$=$CH_3$;
$R_2$=H;
X=methylene;
n=1 or 2;
$R_3$=$R_4$=$R_5$=H;
$R_6$=$CF_3$; and
$R_7$=H.

5. The derivatives according to claim 1, wherein:
$R_1$=$CH_3$;
$R_2$=H;
X represents CH=CH;
n=0 or 1;
$R_3$=$R_4$=$R_5$=H;
$R_6$=$CF_3$ and
$R_7$=H.

6. The derivative according to claim 1, wherein:
$R_1$=$CH_3$;
$R_2$=$R_3$=$R_4$=$R_5$=$R_7$=H;
n=1;
$R_6$=$CF_3$; and X=oxygen.

7. The derivative according to claim 6, wherein the two asymmetric carbon atoms have (R) configuration.

8. A pharmaceutical composition, characterized in that it contains a physiologically acceptable excipient in association with one derivative of formula (I) according to any one of claims 1 to 7.

9. The method of use of the derivatives according to claims 1 to 7 as psychotropic drugs.

* * * * *